United States Patent
Sakuta et al.

(10) Patent No.: US 9,289,372 B2
(45) Date of Patent: Mar. 22, 2016

(54) COSMETIC

(71) Applicant: SHIN-ETSU CHEMICAL CO., LTD., Tokyo (JP)

(72) Inventors: Koji Sakuta, Annaka (JP); Emi Akabane, Annaka (JP); Teruki Ikeda, Cliffside Park, NJ (US)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/588,622

(22) Filed: Jan. 2, 2015

(65) Prior Publication Data
US 2015/0202141 A1  Jul. 23, 2015

(30) Foreign Application Priority Data
Jan. 23, 2014 (JP) ................................. 2014-010541

(51) Int. Cl.
| | |
|---|---|
| C08G 77/12 | (2006.01) |
| A61K 8/894 | (2006.01) |
| A61K 8/891 | (2006.01) |
| A61K 8/92 | (2006.01) |
| A61K 8/34 | (2006.01) |
| A61K 8/37 | (2006.01) |
| A61K 8/06 | (2006.01) |
| A61Q 17/04 | (2006.01) |
| A61Q 5/00 | (2006.01) |
| A61Q 19/00 | (2006.01) |

(52) U.S. Cl.
CPC ................. *A61K 8/894* (2013.01); *A61K 8/064* (2013.01); *A61K 8/345* (2013.01); *A61K 8/37* (2013.01); *A61K 8/891* (2013.01); *A61K 8/92* (2013.01); *A61Q 5/00* (2013.01); *A61Q 17/04* (2013.01); *A61Q 19/00* (2013.01); *A61Q 19/001* (2013.01); *A61Q 19/007* (2013.01); *A61K 2800/10* (2013.01); *A61K 2800/54* (2013.01); *A61K 2800/594* (2013.01); *A61K 2800/95* (2013.01)

(58) Field of Classification Search
CPC ....... C08G 18/48; C08G 77/12; C08G 64/186
See application file for complete search history.

(56) References Cited

U.S. PATENT DOCUMENTS

| | | |
|---|---|---|
| 4,780,145 A | 10/1988 | Mori et al. |
| 4,894,224 A | 1/1990 | Kuwata et al. |
| 5,013,715 A | 5/1991 | Mori et al. |
| 5,236,986 A | 8/1993 | Sakuta |
| 6,444,745 B1 | 9/2002 | Kilgour et al. |
| 6,524,598 B2 | 2/2003 | Sunkel et al. |
| 6,696,049 B2 | 2/2004 | Vatter et al. |
| 2004/0234477 A1 | 11/2004 | Sakuta |
| 2004/0253197 A1* | 12/2004 | Sakuta ................. A61K 8/894 424/70.12 |
| 2006/0034875 A1 | 2/2006 | Nakanishi et al. |
| 2009/0238781 A1 | 9/2009 | Sakuta et al. |
| 2011/0015337 A1 | 1/2011 | Sakuta et al. |
| 2013/0253215 A1 | 9/2013 | Moriya |
| 2013/0287824 A1 | 10/2013 | Inaba |
| 2013/0302263 A1 | 11/2013 | Moriya |

FOREIGN PATENT DOCUMENTS

| | | |
|---|---|---|
| JP | S62-045656 A | 2/1987 |
| JP | S62-054759 A | 3/1987 |
| JP | S62-121764 A | 6/1987 |
| JP | S62-143970 A | 6/1987 |
| JP | S62-143971 A | 6/1987 |
| JP | S62-240335 A | 10/1987 |
| JP | S63-072779 A | 4/1988 |
| JP | S63-159489 A | 7/1988 |
| JP | S63-235366 A | 9/1988 |
| JP | S63-260955 A | 10/1988 |
| JP | H02-43263 A | 2/1990 |
| JP | H04-272932 A | 9/1992 |
| JP | H05-139929 A | 6/1993 |
| JP | H05-140320 A | 6/1993 |
| JP | H05-178733 A | 7/1993 |
| JP | H06-040847 A | 2/1994 |
| JP | H06-040848 A | 2/1994 |
| JP | H06-072826 A | 3/1994 |
| JP | H11-180847 A | 7/1999 |
| JP | 2000-086438 A | 3/2000 |
| JP | 3061434 B2 | 7/2000 |
| JP | 2001-002520 A | 1/2001 |
| JP | 2001-002521 A | 1/2001 |
| JP | 2001-002925 A | 1/2001 |
| JP | 2008-115358 A | 5/2008 |

(Continued)

OTHER PUBLICATIONS

Nomura, Toshio, Chemistry and Chemical Industry, vol. 52 No. 3, pp. 275-277, Mar. 1999.

Jun. 26, 2015 Extended European Search Report issued in European Application No. 15000017.2.

*Primary Examiner* — Kuo-Liang Peng

(74) *Attorney, Agent, or Firm* — Oliff PLC

(57) ABSTRACT

A cosmetic has a polymer (A) having a content of an oxyalkylene unit and/or a glycerin unit of 0.5% by mass or more and under 5.0% by mass; and a polymer (B) having a content of an oxyethylene unit and/or a glycerin unit of 5.0% by mass or more and 20.0% by mass or less, the polymer (A) and the polymer (B) being a crosslinking organopolysiloxane polymer obtained by reacting organohydrogen polysiloxane having two or more hydrogen atoms bonded to a silicon atom in one molecule and polyoxyalkylene and/or polyglycerin having two or more aliphatic unsaturated bonds in one molecule, wherein the mass ratio of the polymer (A) to the polymer (B) is 5:95 to 60:40.

20 Claims, No Drawings

(56) References Cited

FOREIGN PATENT DOCUMENTS

| WO | 03/020828 A1 | 3/2003 |
| WO | 03/024413 A1 | 3/2003 |
| WO | 2004/024798 A1 | 3/2004 |
| WO | 2008/132237 A2 | 11/2008 |

* cited by examiner

COSMETIC

BACKGROUND OF THE INVENTION

1. Field of the Invention

The present invention relates to a cosmetic that contains crosslinking organopolysiloxane having a hydrophilic functional group.

2. Description of the Related Art

Silicone oil has conventionally been used as a base oil in each composition in various fields such as cosmetic production due to its safe and reliable properties. Particularly in skin care and make-up cosmetics, a silicone oil having a low degree of viscosity of 100 mm$^2$/s or less is widely used due to its properties such as excellent spreading properties, light feeling and reliable safety.

However, when, for example, a less fluid composition in the form of a paste is prepared from a low viscous silicone oil using as a base oil, it is necessary to use organic materials such as dextrin fatty acid ester (Patent Documents 1 to 4), sucrose fatty acid ester (Patent Document 5), trimethyl-silylated polyvinyl alcohol and trimethyl-silylated polysaccharide (Patent Document 6) and fatty acid ester group-containing cellulose ether (Patent Document 7), and organic modified clay minerals (Patent Documents 8 to 10) as a thickner. Nevertheless, conventional techniques fail to achieve a smooth and uniform composition in a cosmetic and maintain storage stability so as not to cause separation or discharge of a low viscous silicone oil.

To solve the problem, a method for obtaining a uniform composition in the form of a paste by using specific organopolysiloxane as a thickner and treating it with a low viscous silicone oil by shear force, was proposed (Patent Document 11). In addition, a composition obtained by introducing a long chain alkyl moiety to a molecule of a crosslinking organopolysiloxane used as a thickner to provide the same characteristics for a hydrocarbon oil and an ester oil was proposed (Patent Document 12).

Meanwhile, skin care and make-up cosmetics mostly include an emulsified composition blended with required components of not only an oil content but also moisture, and emulsified compositions are classified into oil-in-water, water-in-oil and multilayer emulsified compositions according to the type of blending. A composition using the above crosslinking organopolysiloxane as a thickner was certainly excellent in the effect of stably dispersing oil materials such as a silicone oil, a hydrocarbon oil and an ester oil, but failed to provide an emulsified composition in which water was also dispersed.

To solve the technical problem, a composition in which a polyoxyalkylene moiety is introduced in a molecule of crosslinking organopolysiloxane was proposed to obtain a stable water-in-oil emulsified composition (Patent Documents 13 and 14). Also, a composition that can solve the problem of odor found over time (Patent Document 15) and a composition in which polyglycerin moiety is introduced as a hydrophilic group (Patent Document 16) were proposed. In addition, a crosslinking organopolysiloxane capable of obtaining a favorable emulsified composition, even using a silicone oil and an organic oil such as a hydrocarbon oil and an ester oil as an oil material at the same time, was developed (Patent Document 17).

Such a crosslinking organopolysiloxane having a hydrophilic group in its molecule provides both a swelling property for an oil material and a water emulsifying property. Although the particle diameter for water dispersion is 10 to 20 μm, which is normally difficult to maintain storage stability, a water-in-oil emulsified composition excellent in storage stability can be obtained from the crosslinking organopolysiloxane (Non-Patent Document 1), and cosmetic compositions using this characteristic were proposed (Patent Documents 13, and 18 to 24).

Another characteristic in the crosslinking organopolysiloxane is to obtain a water-in-oil emulsified composition having a high inner water phase ratio (Patent Documents 25 to 27). In order to obtain a water-in-oil emulsified composition having a further improved thixotropy property of an oil phase, a cosmetic composition using both crosslinking organopolysiloxane having a hydrophilic group and crosslinking organopolysiloxane having no hydrophilic group was also proposed (Patent Documents 28 and 29).

PRIOR ART DOCUMENTS

Patent Documents

Patent Document 1: Japanese Patent Laid-Open Publication No. S62-121764
Patent Document 2: Japanese Patent Laid-Open Publication No. S62-143970
Patent Document 3: Japanese Patent Laid-Open Publication No. S62-143971
Patent Document 4: Japanese Patent Laid-Open Publication No. S63-159489
Patent Document 5: Japanese Patent Laid-Open Publication No. S63-235366
Patent Document 6: Japanese Patent Laid-Open Publication No. S62-240335
Patent Document 7: Japanese Patent Laid-Open Publication No. S63-260955
Patent Document 8: Japanese Patent Laid-Open Publication No. S62-045656
Patent Document 9: Japanese Patent Laid-Open Publication No. S62-054759
Patent Document 10: Japanese Patent Laid-Open Publication No. S63-072779
Patent Document 11: Japanese Patent Laid-Open Publication No. H02-043263
Patent Document 12: WO2003/024413
Patent Document 13: Japanese Patent Laid-Open Publication No. H04-272932
Patent Document 14: Japanese Patent Laid-Open Publication No. H05-140320
Patent Document 15: WO2003/020828
Patent Document 16: WO2004/024798
Patent Document 17: Japanese Patent Laid-Open Publication No. 2008-115358
Patent Document 18: Japanese Patent Laid-Open Publication No. H05-139929
Patent Document 19: Japanese Patent Laid-Open Publication No. H05-178733
Patent Document 20: Japanese Patent Laid-Open Publication No. H06-040847
Patent Document 21: Japanese Patent Laid-Open Publication No. H06-040848
Patent Document 22: Japanese Patent Laid-Open Publication No. H06-072826
Patent Document 23: Japanese Patent Laid-Open Publication No. H11-180847
Patent Document 24: Japanese Patent Laid-Open Publication No. 2000-086438
Patent Document 25: Japanese Patent Laid-Open Publication No. 2001-002520

Patent Document 26: Japanese Patent Laid-Open Publication No. 2001-002521

Patent Document 27: Japanese Patent Laid-Open Publication No. 2001-002925

Patent Document 28: U.S. Pat. No. 6,524,598

Patent Document 29: U.S. Pat. No. 6,696,049

Non-Patent Document

Non-Patent Document 1: Toshio Nomura, Chemistry and Industry (Kagaku-to-Kohgyo), 52, 3, 275-277 (1999)

SUMMARY OF THE INVENTION

A water-in-oil emulsified composition using the above crosslinking organopolysiloxane having a hydrophilic group in its molecule, due to an ability to increase the ratio of an inner water phase and its large diameter of emulsified particles of inner phase water, is characterized by an extremely shorter "playing time," and can obtain a cosmetic having a high light feeling as found in an oil-in-water emulsified composition. "Playing time" refers to the time from start of coating a cosmetic on the skin to the change in feeling of the cosmetic extended on the skin. This change in feeling is attributed to a favorable storage stability with the emulsified particle diameter remaining large, and to immediate destruction of emulsified particles of an inner water phase when a cosmetic is coated on the skin to separate the inner water phase on the skin surface.

When the playing time is too short, it can be adjusted by using a linear emulsifier having no crosslinking structure as well to make the emulsified particle diameter smaller. However, while the emulsified particle diameter becomes smaller and the playing time becomes longer in proportion to the blending ratio of the linear emulsifier, the degree of change in feeling also becomes smaller in proportion to the blending ratio.

Therefore, a water-in-oil emulsified composition that can make only the playing time longer, with the degree of change in feeling remaining large, is strongly desired. The above Patent Documents 15 and 16 disclose an advantage of obtaining a stable emulsified composition, but fail to suggest means for obtaining a favorable playing time. In addition, a method for using both an emulsion crosslinking organopolysiloxane and a non-emulsion crosslinking organopolysiloxane cannot solve the above problems.

The present invention was made to solve the problems mentioned above, and was intended to provide a cosmetic, particularly a water-in-oil emulsified cosmetic, having a large degree of change in feeling and a longer playing time, in which the spreadability of an outer oil phase is favorably provided until the completion of uniformly coating of a cosmetic on the skin and a light feeling due to separation of water phase is certainly given just after completion of coating of a cosmetic.

To solve the problems mentioned above, the present invention provides a cosmetic comprising a polymer (A) having a content of an oxyalkylene unit and/or a glycerin unit of 0.5% by mass or more and under 5.0% by mass; and a polymer (B) having a content of an oxyethylene unit and/or a glycerin unit of 5.0% by mass or more and 20.0% by mass or less, the polymer (A) and the polymer (B) being a crosslinking organopolysiloxane polymer obtained by reacting organohydrogen polysiloxane having two or more hydrogen atoms bonded to a silicon atom in one molecule and polyoxyalkylene and/or polyglycerin having two or more aliphatic unsaturated bonds in one molecule in the presence of a catalyst for a hydrosilylation reaction, wherein a mass ratio of the polymer (A) to the polymer (B) is 5:95 to 60:40.

Since the cosmetic contains two types of polymers: a crosslinking organopolysiloxane polymer having a low content of a hydrophilic group unit and a crosslinking organopolysiloxane polymer having a high content of a hydrophilic group unit with a mass ratio of 5:95 to 60:40, the playing time can be made longer without immediately destroying emulsified particles of inner phase water. Further, the cosmetic, particularly as a water-in-oil emulsified cosmetic, can provide larger storage stability of emulsion and a favorable coating property which provides a large degree of change in feeling.

In these cases, it is preferred that the first crosslinking organopolysiloxane polymer of the polymer (A) and the second crosslinking organopolysiloxane polymer of the polymer (B) are each obtained by subjecting an organohydrogen polysiloxane represented by the following general formula (I) and one or more compounds selected from the group consisting of a polyoxyalkylene compound represented by the following general formulae (II), (III), or (IV) and a polyglycerin compound represented by the following general formula (V) to addition polymerization, are insoluble in an organic solvent, and swell by containing a liquid oil, an amount of which is own weight or more of the crosslinking organopolysiloxane polymer, $$R^1{}_a H_c Si_{(4-a-c)/2} \tag{I}$$

$$C_d H_{2d-1} O(C_e H_{2e} O)_f C_d H_{2d-1} \tag{II}$$

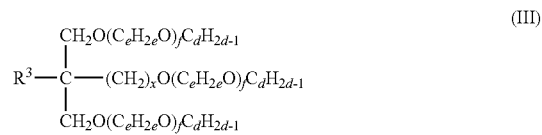

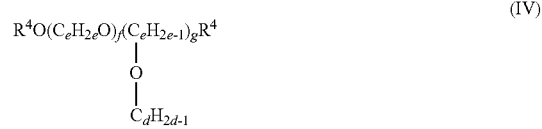

$$C_d H_{2d-1} O(CH_2 CH(OH) CH_2 O)_h C_d H_{2d-1} \tag{V}$$

wherein each $R^1$ independently represents the same or different substituted or unsubstituted monovalent hydrocarbon group having 1 to 30 carbon atoms having no alkenyl group; $R^3$ represents a substituted or unsubstituted monovalent hydrocarbon group having 1 to 10 carbon atoms having no hydrogen atom or alkenyl group; each $R^4$ independently represents the same or different organic group represented by $-C_d H_{2d-1}$ or the same as $R^3$; "a" and "c" represent a positive number satisfying $1.0 \leq a \leq 2.3$ and $0.001 \leq c \leq 1.0$, respectively, and also satisfying $1.5 \leq a+c \leq 2.6$; "d" represents an integer of 2 to 6; "e" represents an integer of 2 to 4; "f" represents an integer of 1 to 200; "g" represents an integer of 1 to 20; "h" represents an integer of 2 to 10; and "x" represents 0 or 1.

Such a cosmetic can provide both more desirable storage stability of emulsion and a favorable coating property.

In these cases, it is preferred that the polymer (A) and the polymer (B) are each obtained by subjecting the organohydrogen polysiloxane (I) and the polyoxyalkylene compound (II) or the polyglycerin compound (V) to addition polymerization, wherein the content of an oxyethylene and/or a glycerin unit in the polymer (A) is 0.5% by mass or more and under 5.0% by mass.

Such a cosmetic can provide a larger degree of change in feeling and a favorable coating property.

The cosmetic preferably comprises the polymer (A) and the polymer (B), with a total content being 1.0% by mass or more and 50% by mass or less, relative to a total amount of the cosmetic.

Such a cosmetic can provide both storage stability and a favorable coating property without losing characteristics as a water-in-oil cosmetic.

The present invention provides a cosmetic that preferably further contains water and is in a form of an emulsion, wherein the emulsion is more preferably in a form of a water-in-oil.

Such a cosmetic can be used according to various uses.

Also, the present invention provides a cosmetic that preferably further contains one or more types of a silicone oil, a hydrocarbon oil, a glycol, an ester oil, a glyceride oil and a UV absorbing-scattering agent.

The cosmetic of the present invention can contain different types of additives according to uses.

The present invention provides a cosmetic that preferably further contains a powder in a form of a liquid, a paste or a solid, with the powder dispersed therein.

Accordingly the cosmetic of the present invention can be made so that a powder is dispersed and various types of appearances and forms can be determined according to uses.

As stated above, the cosmetic according to the present invention can provide favorable storage stability, extremely excellent sense of touch in use consisting of high light feeling equal to an oil-in-water emulsified cosmetic is provided even in the form of a water-in-oil emulsified cosmetic, a longer playing time and a favorable coating property such that favorable spreadability due to an effect of an oil-based component while coating is given and change in feeling due to separation of a water phase component after completion of coating is given.

DETAILED DESCRIPTION OF THE PREFERRED EMBODIMENTS

Inventors of the present invention have carried out extended research to find out a cosmetic, particularly a water-in-oil emulsified cosmetic, having favorable storage stability and desired playing time, the cosmetic comprising a polymer (A) with a content of an oxyalkylene unit and/or a glycerin unit of 0.5% by mass or more and under 5.0% by mass in the polymer and a polymer (B) with a content of an oxyethylene unit and/or a glycerin unit of 5.0% by mass or more and 20.0% by mass or less in the polymer to be blended, the polymer (A) and the polymer (B) being a crosslinking organopolysiloxane polymer having a polyoxyalkylene group and/or a polyglycerin group in its molecule, wherein the mass ratio of the polymer (A) to the polymer (B) is 5:95 to 60:40. Based on that information, the present invention was accomplished.

The present invention will be described in more detail.

The cosmetic of the present invention can be obtained by blending one or more types of a polymer (A) having a content of an oxyalkylene unit and/or a glycerin unit of 0.5% by mass or more and under 5.0% by mass and one or more types of a polymer (B) having a content of an oxyethylene unit and/or a glycerin unit of 5.0% by mass or more and 20.0% by mass or less, the polymer (A) and the polymer (B) being a crosslinking organopolysiloxane polymer obtained by reacting organohydrogen polysiloxane having two or more hydrogen atoms bonded to a silicon atom in one molecule and polyoxyalkylene and/or polyglycerin having two or more aliphatic unsaturated bonds in one molecule in the presence of a catalyst for a hydrosilylation reaction.

The organohydrogen polysiloxane is preferably represented by the general formula (I), $$R^1_a H_c Si_{(4-a-c)/2} \quad (I)$$

wherein each $R^1$ independently represents the same or different substituted or unsubstituted monovalent hydrocarbon group having 1 to 30 carbon atoms having no alkenyl group; "a" and "c" represent a positive number satisfying $1.0 \le a \le 2.3$ and $0.001 \le c \le 1.0$, respectively, and also satisfying $1.5 \le a + c \le 2.6$.

Illustrative example of the $R^1$ includes an alkyl group such as a methyl group, an ethyl group, a propyl group, a butyl group, a pentyl group, a hexyl group, a heptyl group, an octyl group, a nonyl group, and a decyl group; a saturated alicyclic hydrocarbon group such as a cyclopentyl group, and a cyclohexyl group; an aryl group such as a phenyl group, and a tolyl group; and a fluorine-substituted alkyl group such as a trifluoropropyl group, a nonafluorohexyl group, and a heptadecyl fluorodecyl group.

"a" represents 1.0 to 2.3, preferably 1.2 to 2.1, and "c" represents 0.001 to 1.0, preferably 0.005 to 0.5. When "a" represents 1.0 or more, the degree of crosslinking is not excessively increased to contain a liquid oil, the amount of which is own weight or more of the crosslinking organopolysiloxane polymer. When "a" represents 2.3 or less, the degree of crosslinking is not excessively decreased to easily form a three-dimensional crosslinking structure. When "c" represents 0.001 or more, the degree of crosslinking is not excessively decreased to easily form a three-dimensional crosslinking structure. When "c" represents 1.0 or less, the degree of crosslinking is not excessively increased to contain a liquid oil, the amount of which is own weight or more of the crosslinking organopolysiloxane polymer. a+c represents 1.5 to 2.6, preferably 1.8 to 2.2.

The organohydrogen polysiloxane may be a linear, a branched, or a cyclic structure, but in order to achieve smooth polymerization reaction, it preferably consists of a linear unit, or mainly a linear unit and partially a branched unit.

Moreover, according to a method shown in Patent Document 17, an organopolysiloxane unit may be grafted into a skeleton of a crosslinking organopolysiloxane polymer.

One or more types of polyoxyalkylene compounds represented by the general formulae (II), (III), and (IV) are preferably be used, $$C_d H_{2d-1} O(C_e H_{2e} O)_f C_d H_{2d-1} \quad (II)$$

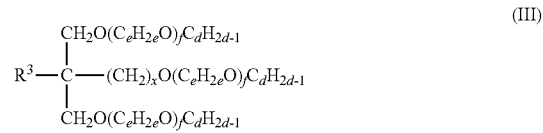

(III)

(IV)

wherein $R^3$ represents a substituted or unsubstituted monovalent hydrocarbon group having 1 to 10 carbon atoms having no hydrogen atom or alkenyl group; each $R^4$ independently represents the same or different organic group represented by $—C_dH_{2d-1}$ or the same as $R^3$ "d" represents an integer of 2 to 6; "e" represents an integer of 2 to 4; "f" represents an integer of 1 to 200; "g" represents an integer of 1 to 20; and "x" represents 0 or 1.

Illustrative example of the $R^3$ preferably includes, in addition to a hydrogen atom, a methyl group, an ethyl group, a propyl group, a butyl group, a pentyl group, a hexyl group, a heptyl group, an octyl group, a nonyl group, and a decyl group, but particularly preferably a hydrogen atom, a methyl group, an ethyl group, and a propyl group.

A compound represented by the formula (III) can be obtained, e.g. by using glycerin or trimethylol propane as a starting material and adding alkylene oxide thereto to alkenyl-etherify an end thereof. The compound, having 3 polyoxyalkylene end groups that are all alkenyl-etherified: the two are blocked by alkenyl ether and the other remaining one is still a hydroxyl group, can be used.

When the compound is obtained by using glycerin monoallyl ether and trimethylol propane monoallyl ether as a starting material and adding alkylene oxide thereto to alkenyl-etherify an end thereof, the polyoxyalkylene compound, containing 2 polyoxyalkylene units in one molecule and 3 end alkenyl groups in one molecule, can also be used.

$R^4$ represents the same as $R^3$ or an organic group represented by $—C_dH_{2d-1}$. The compound represented by the formula (IV) can be obtained, e.g. by adding alkylene oxide and allyl glycidyl ether to a lower alcohol or an allyl alcohol, or thereafter subjecting an end thereof to alkyl- or alkenyl-etherify the same.

Each "d" independently represents an integer of 2 to 6, preferably an integer of 3 to 6. Each "e" independently represents an integer of 2 to 4, and one or more types of an ethylene oxide unit, a propylene oxide unit, and a butylene oxide unit are selected as $(C_eH_{2e}O)$ unit. "f" represents an integer of 1 to 200, preferably 3 to 100. "g" represents an integer of 1 to 20, but when $R^4$ are both an organic group represented by $—C_dH_{2d-1}$, "g" preferably represents an integer of 1 to 10 to easily form a three-dimensional crosslinking structure, and when $R^4$ are both the same as $R^3$, "g" preferably represents an integer of 2 to 20, more preferably an integer of 3 to 10 to easily form a three-dimensional crosslinking structure. "x" represents 0 or 1.

The polyglycerin compound is represented by the general formula (V), $$C_dH_{2d-1}O(CH_2CH(OH)CH_2O)_hC_dH_{2d-1} \quad (V)$$

wherein "d" represents the same as before, "h" represents an integer of 2 to 10, preferably an integer of 3 to 6. The polyglycerin compound may be a linear, a branched, or a cyclic structure, but in order to achieve smooth polymerization reaction, it may consist of a linear unit, or mainly a linear unit and partially a branched unit.

The polymer (A) consisting of a crosslinking organopolysiloxane polymer has a content of an oxyalkylene unit and/or a glycerin unit of 0.5% by mass or more and under 5.0% by mass, and the polymer (B) consisting of a crosslinking organopolysiloxane polymer has a content of an oxyethylene unit and/or a glycerin unit of 5.0% by mass or more and 20.0% by mass or less. The oxyalkylene unit refers to the total amount of e.g. an oxyethylene unit, an oxypropylene unit, and an oxybutylene unit. The calculation method will be described with reference to the following examples.

When the organohydrogen polysiloxane is represented by the following general formula,

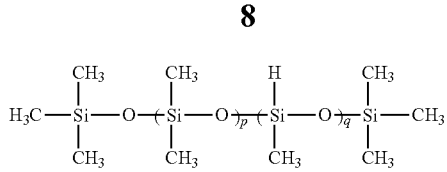

the molecular weight is calculated by the following formula.

Molecular weight=$162+74p+60q$ [A]

When the polyoxyalkylene compound is represented by the following general formula, $$CH_2=CHCH_2-O-(C_2H_4O)_r-(C_3H_6O)_s-CH_2CH=CH_2$$

the molecular weight, the content of an oxyalkylene unit, and the content of an oxyethylene unit are obtained by the following formulae.

Molecular weight=$98+44 \times r+58 \times s$ [B]

Content of an oxyalkylene unit=$44 \times r+58 \times s$ [C]

Content of an oxyethylene unit=$44 \times r$ [D]

Assuming that the charged molar ratio of a polyoxyalkylene compound to organohydrogen polysiloxane is $z_1$, and the charged molar ratio of a polyoxyethylene compound to organohydrogen polysiloxane is $z_2$, the content of an oxyalkylene unit (% by mass) and the content of an oxyethylene unit (% by mass) in the crosslinking organopolysiloxane polymer can be obtained by the following formulae, respectively.

Content of an oxyalkylene unit=$[C] \times z_1/([B] \times z_1+[A]) \times 100$

Content of an oxyethylene unit=$[D] \times z_2/([B] \times z_2+[A]) \times 100$

Likewise, when the polyglycerin compound is represented by the following general formula, $$CH_2=CHCH_2-O-(CH_2CH(OH)CH_2O)_t-CH_2CH=CH_2$$

the molecular weight and the content of glycerin unit are obtained by the following formulae.

Molecular weight=$98+74 \times t$ [E]

Content of a glycerin unit=$74 \times t$ [F]

Assuming that the charged molar ratio of a polyglycerin compound to organohydrogen polysiloxane is $z_3$, the content of a glycerin unit (% by mass) in the crosslinking organopolysiloxane polymer can be obtained by the following formula.

Content of a glycerin unit=$[F] \times z_3/([E] \times z_3+[A]) \times 100$

When the polymer (A) consisting of a crosslinking organopolysiloxane polymer contains both an oxyalkylene unit and a glycerin unit, the content of the oxyalkylene unit and the glycerin unit can be calculated by the following formula according to the above formula.

Content of oxyalkylene unit and glycerin unit=$([C] \times z_1+[F] \times z_3)/([B] \times z_1+[E] \times z_3+[A]) \times 100$ When the polymer (A) and/or the polymer (B) each consisting of a crosslinking organopolysiloxane polymer contain both an oxyethylene unit and a glycerin unit, the content of the oxyethylene unit and the glycerin unit can be calculated by the following formula according to the above formula.

Content of oxyethylene unit and glycerin unit=$([D] \times z_2+[F] \times z_3)/([B] \times z_2+[E] \times z_3+[A]) \times 100$ In the polymer (A) consisting of a crosslinking organopolysiloxane polymer, the content of an oxyalkylene unit and/or a glycerin unit is 0.5% by mass or more and under 5.0% by mass. When the content is under 0.5% by mass, the adjusting effect of the playing time is not found any more, and when it exceeds 5.0% by mass, the component will be the same as the polymer (B), resulting in no adjusting effect of playing time as well.

The polymer (A) and the polymer (B) are preferably obtained by subjecting the organohydrogen polysiloxane (I) and the polyoxyalkylene compound (II) or the polyglycerin compound (V) to addition polymerization. The content of an oxyethylene and/or a glycerin unit in the polymer (A) is preferably 0.5% by mass or more and under 5.0% by mass.

The cosmetic containing the above polymer can provide a larger degree of change in feeling and a favorable coating property.

In the polymer (B) consisting of a crosslinking organopolysiloxane polymer, the content of an oxyethylene unit and/or a glycerin unit is 5.0% by mass or more and 20.0% by mass or less. The method for calculating the content is the same as before. When the unit content is under 5.0% by mass, the emulsion stability becomes lower, and when it exceeds 20.0% by mass, the emulsion stability becomes lower as well. Since the polymer (B) is a component that can encourage emulsion stability, a sufficient stability cannot be obtained if the content of a hydrophilic oxyethylene unit is not within the above range.

The mass ratio of the polymer (A) to the polymer (B) is 5:95 to 60:40. When the mass ratio of the polymer (A) is under 5, the adjusting effect of the playing time cannot be obtained and when it exceeds 60, the emulsion stability becomes lower.

Since the cosmetic of the present invention contains two types of polymers: a crosslinking organopolysiloxane polymer having a low content of a hydrophilic group unit and a crosslinking organopolysiloxane polymer having a high content of a hydrophilic group unit with a mass ratio of 5:95 to 60:40, the playing time can be made longer without immediately destroying emulsified particles of inner phase water. Further, the cosmetic, particularly as a water-in-oil emulsified cosmetic, can provide both larger storage stability of emulsion and a favorable coating property which provides a large degree of change in feeling.

To obtain the crosslinking organopolysiloxane polymer of the present invention, the reaction may be performed in the presence of a catalyst for a hydrosilylation reaction such as a platinum compound (e.g. chloroplatinic acid, an alcohol-modified chloroplatinic acid, and a chloroplatinic acid-divinylsiloxane complex, and so on) and a rhodium compound at room temperature or at a higher temperature (approx. 50 to 120° C.)

The reaction may be performed in the absence of solvent or in the presence of a liquid oil material. An organic solvent may also be used as required. Illustrative example of the organic solvent includes an aliphatic alcohol such as methanol, ethanol, 2-propanol, and butanol; an aromatic hydrocarbon such as benzene, toluene, and xylene; an aliphatic or alicyclic hydrocarbon such as n-pentane, n-hexane, and cyclohexane; a halogenated hydrocarbon such as dichloromethane, chloroform, and carbon tetrachloride; and a ketone solvent such as acetone, and methylethyl ketone. However, the reaction is preferably solventless, or by using ethanol or 2-propanol due to cosmetic use.

According to the methods disclosed in Patents 15 and 16, a deodorization process may be used.

The above method can maintain a stable quality due to easy control of the ratio of partial addition reaction.

Meanwhile, a method for obtaining a crosslinking organopolysiloxane polymer includes a method for reacting an organohydrogen polysiloxane having a polyoxyalkylene group or a polyglycerin group in its molecule and a compound having two or more unsaturated groups and having no polyoxyalkylene group or polyglycerin group in its molecule, such as organovinyl polysiloxane, $\alpha,\omega$-alkenyl diene, and polyoxypropylene diallyl ether. In this case, in order to obtain organohydrogen polysiloxane having a polyoxyalkylene group or a polyglycerin group in its molecule, it is necessary to subject a polyoxyalkylene compound or a polyglycerin compound having one unsaturated group in its molecule to partial addition reaction to organohydrogen polysiloxane to leave an Si—H group required for crosslinking reaction. However, this method fails to control the ratio of partial addition reaction and it is difficult to maintain a stable product quality.

The crosslinking organopolysiloxane polymer of the present invention can have a three-dimensional crosslinking structure that is insoluble in an organic solvent and can swell by containing a liquid oil, the amount of which is own weight or more of the polymer. The organic solvent refers to an aliphatic organic solvent such as a linear or a branched pentane, hexane, decane, dodecane, hexadecane, and octadecane; an aromatic organic solvent such as benzene, toluene, and xylene; an alcohol organic solvent such as methanol, ethanol, propanol, butanol, hexanol, and decanol; a halogenated organic solvent such as chloroform, and carbon tetrachloride; a ketone organic solvent such as acetone, and methylethyl ketone; and a silicone solvent such as low viscous dimethyl polysiloxane, methyl phenyl polysiloxane, and cyclic dimethyl polysiloxane, and the polymer is not uniformly dissolved in any organic solvent.

The cosmetic containing the above polymer can provide both more favorable storage stability of emulsion and a favorable coating property.

In addition, the crosslinking organopolysiloxane polymer of the present invention is preferably mixed with a liquid oil and then kneaded by shear force to make a composition in the form of a paste and to be blended into a cosmetic. Illustrative example of an apparatus for kneading the polymer and the liquid oil includes a 3-roll mill, a 2-roll mill, a side grinder, a colloid mill, a Gaulin homogenizer, and a disperser. In addition, another apparatus having the similar or same function may be used.

The cosmetic of the present invention preferably contains the polymer (A) and the polymer (B), with a total content being 1.0% by mass or more and 50% by mass or less, relative to a total amount of the cosmetic.

Such a cosmetic can provide both storage stability and a favorable coating property without losing characteristics as a water-in-oil cosmetic.

Into the cosmetic of the present invention can be blended one, or two or more, of oil materials depending on its purpose. An oil material in any form of a solid, a semi-solid, and a liquid can be used provided that it is used in a usually used cosmetic.

Illustrative example of the natural vegetable and animal fatty oil and the semi-synthetic oil includes an avocado oil, a linseed oil, an almond oil, an insects wax, a perilla oil, an olive oil, a cacao butter, a kapok wax, a kaya oil, a carnauba wax, a lever oil, a candelilla wax, a purified candelilla wax, a beef tallow, a neats-foot oil, a beef bone fat, a cured beef tallow, an apricot kernel oil, a whale wax, a hydrogenated oil, a wheat germ oil, a sesame oil, a rice germ oil, a rice bran oil, a sugarcane wax, a sasanqua oil, a safflower oil, a shea butter, a Chinese tung oil, a cinnamon oil, a jojoba wax, a squalane oil, a squalene oil, a shellac wax, a turtle oil, a soybean oil, a tea seed oil, a camellia oil, an evening primrose oil, a corn oil, a pig fat, a rapeseed oil, a Japanese tung oil, a bran wax, a germ oil, a horse wax, a persic oil, a palm oil, a palm kernel oil, a castor oil, a cured castor oil, a methyl ester of castor oil fatty acid, a sunflower oil, a grape seed oil, a bayberry wax, a jojoba oil, a macadamia nut oil, a bees wax, a mink oil, a meadow foam oil, a cotton seed oil, a cotton wax, a Japan wax, a Japan wax kernel oil, a montan wax, a coconut oil, a cured coconut oil, a tri-coconut fatty acid glyceride, a mutton tallow, a peanut oil, lanolin, liquid lanolin, reduced lanolin, lanolin alcohol, hard lanolin, lanolin acetate, lanolin alcohol acetate, isopropyl lanolin fatty acid, POE lanolin alcohol ether, POE lanolin alcohol acetate, polyethylene glycol lanolin fatty acid, POE hydrogenated lanolin alcohol ether, and an egg-yolk oil. Meanwhile, POE means polyoxyethylene. The same is applied to the following cases.

Illustrative example of the hydrocarbon oil includes a linear, a branched, and a volatile hydrocarbon oil. Illustrative example of the hydrocarbon oil includes an ozocerite, an α-olefin oligomer, a light isoparaffin, an isododecane, an isohexadecane, a light liquid isoparaffin, a squalane, a synthetic squalane, a vegetable squalane, a squalene, a ceresin, a paraffin, paraffin wax, a polyethylene wax, a polyethylene/polypropylene wax, an (ethylene/propylene/styrene) copolymer, a (butylene/propylene/styrene) copolymer, a liquid paraffin, a liquid isoparaffin, a pristane, a polyisobutylene, a hydrogenerated polyisobutene, a microcrystalline wax, and a vaseline. Illustrative example of the higher fatty acids includes a lauric acid, a myristic acid, a palmitic acid, a stearic acid, a behenic acid, an undecylenic acid, an oleic acid, a linoleic acid, a linolenic acid, an arachidonic acid, an eicosapentaenoic acid (EPA), a docosahexaenoic acid (DHA), an isostearic acid, and a 12-hydroxystearic acid.

Illustrative example of the higher alcohol includes a lauryl alcohol, a myristyl alcohol, a palmityl alcohol, a stearyl alcohol, a behenyl alcohol, a hexadecyl alcohol, an oleyl alcohol, an isostearyl alcohol, a hexyl dodecanol, an octyl dodecanol, a cetostearyl alcohol, a 2-decyl tetradecynol, a cholesterol, a phytosterol, a POE cholesterol ether, a monostearyl glycerin ether (batyl alcohol), and a monooleyl glyceryl ether (selachyl alcohol).

Illustrative example of the ester oil includes diisobutyl adipate, 2-hexyldecyl adipate, di-2-heptylundecyl adipate, an N-alkylglycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyl dodecyl gum ester, oleyl oleate, octyldodecyl oleate, decyl oleate, neopentyl glycol dioctanoate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isononyl isononanoate, isotridecyl isononanoate, isopropyl palmitate, 2-ethylhexyl palmitate, 2-hexyldecyl palmitate, 2-heptylundecyl palmitate, cholesteryl 12-hydroxystearate, a dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate ester, isopropylester lauroyl sarcosinate, and diisostearyl malate. Illustrative example of the glyceride oil includes acetoglyceryl, glyceryl triisooctanoate, glyceryl triisostearate, glyceryl triisopalmitate, glyceryl tribehenate, glyceryl monostearate, glyceryl di-2-heptylundecanoate, glyceryl trimyristate and diglyceryl myristate isostearate.

Illustrative example of the silicone oil includes low viscous to high viscous linear or branched organopolysiloxanes such as dimethyl polysiloxane, tristrimethyl siloxymethylsilane, caprylyl methicone, phenyl trimethicone, tetrakis trimethylsiloxysilane, methyl phenyl polysiloxane, methylhexyl polysiloxane, methyl hydrogen polysiloxane, and dimethylsiloxane/methylphenylsiloxane copolymer; a cyclic organopolysiloxane such as octamethyl cyclotetrasiloxane, decamethyl cyclopentasiloxane, dodecamethyl cyclohexasiloxane, tetramethyl tetrahydrogen cyclotetrasiloxane, and tetramethyltetraphenyl cyclotetra siloxane; a silicone rubber such as an amino-modified organopolysiloxane, a pyrrolidone-modified organopolysiloxane, a pyrrolidone carboxylate-modified organopolysiloxane, a gum dimethyl polysiloxane with a high degree of polymerization, gum amino-modified organopolysiloxane, and gum dimethylsiloxane/methylphenylsiloxane copolymer; a silicone gum and rubber cyclic organopolysiloxane solution, a trimethylsiloxysilicate, a trimethylsiloxysilicate cyclicsiloxane solution, higher alkoxy-modified silicone such as stearoxysilicone, a higher fatty acid-modified silicone, an alkyl-modified silicone, a long chain alkyl-modified silicone, an amino acid-modified silicone, a fluorine-modified silicone, a silicone resin and a melt of a silicone resin. Illustrative example of the fluorinated oil material includes perfluoro polyether, perfluoro decalin, and perflouro octane.

Amount of these oil materials to be blended is dependent on the type of the materials, but it is preferably in the range of 1 to 60% by mass, relative to a total amount of the cosmetic.

The cosmetic of the present invention may use, depending on the purpose thereof, one, or two or more types of compounds having an alcoholic hydroxyl group in a molecular structure.

Illustrative example of the compound having an alcohol hydroxyl group that can be added in the present invention includes a lower alcohol such as ethanol and isopropyl alcohol; a sugar alcohol such as sorbitol and maltose; a sterol such as cholesterol, sitosterol, phytosterol, and lanosterol; and a polyvalent alcohol such as butyleneglycol, propyleneglycol, dibutyleneglycol, and pentylene glycol. The amount to be blended is preferably the range of 0.1 to 50% by mass, relative to a total amount of the cosmetic.

The cosmetic of the present invention may use, depending on the purpose thereof, one or more types of water-soluble or water-swelling polymers.

Illustrative example thereof includes a plant polymer such as an Arabia gum, tragacanth, galactan, a carob gum, a guar gum, a karaya gum, carrageenan, pectin, agar, quince seed (marmelo), starch (rice, corn, potato, wheat, and so on), an algae colloid, a trant gum, a locust bean gum; a microbial polymer such as a xanthan gum, dextran, succinoglucan, and pullulan; an animal polymer such as collagen, casein, albumin, and gelatin; a starch polymer such as carboxymethyl starch and methyl hydroxypropyl starch; a cellulose polymer such as methyl cellulose, ethyl cellulose, methyl hydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose, and cellulose; an alginic acid polymer such as sodium alginate and propylene glycol alginate ester; a vinyl polymer such as polyvinyl methyl ether and carboxy vinyl polymer; a polyoxyethylene polymer; a polyoxyethylene polyoxypropylene copolymer; an acryl polymer such as sodium polyacrylate, polyethyl acrylate, polyacrylamide, and an acryloyldimethyl taurate salt copolymer; other synthetic water-soluble polymer such as polyethyleneimine and a cationic polymer; and an inorganic water-soluble polymer such as bentonite, aluminum magnesium silicate, montmorillonite, beidellite, nontronite, saponite, hectorite, and anhydrous silicic acid. Examples of these water-soluble polymers also include a film-forming agent such as a polyvinyl alcohol and a polyvinyl pyrrolidone. Amount of these polymers to be blended is preferably in the range of 0.1 to 25% by mass, relative to a total amount of the cosmetic.

The cosmetic of the present invention may use, depending on the purpose thereof, one, or two or more types of powders and/or colorants. As to the powder like this, any powder may be used regardless of its form (spherical, needle-like, plate-like, and so on), its particle diameter (fumed, microparticle, pigment-class, and so on), and its particle structure (porous, non-porous, and so on), provided that the powder is used in a usual cosmetic. Illustrative example of the powder includes an inorganic powder, an organic powder, a surfactant metal salt powder, a color pigment, a pearl pigment, a metal powder pigment, a tar dye, and a natural dye.

Illustrative example of the inorganic powder includes titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, golden mica, pink mica, black mica, lithia mica, silicic acid, anhydrous silicic acid, aluminum silicate, magnesium silicate, aluminum magnesium silicate, calcium silicate, barium silicate, strontium silicate, a metal tungstate salt, hydroxy apatite, vermiculite, higilite, bentonite, montmorillonite, hectorite, zeolite, ceramics powder, dibasic calcium phosphate, alumina, aluminum hydroxide, boron nitride, and silica.

Illustrative example of the organic powder includes a polyamide powder, a polyester powder, a polyethylene powder, a polypropylene powder, a polystyrene powder, a polyurethane powder, a benzoguanamine powder, a polymethyl benzoguanamine powder, a tetrafluoroethylene powder, a polymethyl methacrylate powder, a cellulose powder, a silk powder, a nylon powder such as a 12 nylon powder and a 6 nylon powder, a silicone powder, a styrene-acrylic acid copolymer, a divinyl benzene-styrene copolymer, a vinyl resin, a urea resin, a phenolic resin, a fluorinated resin, a silicone resin, an acryl resin, a melamine resin, an epoxy resin, a polycarbonate resin, a fine crystalline fiber powder, a starch powder, and lauroyl lysine.

Illustrative example of the surfactant metal salt powder (metal soap) includes zinc stearate, aluminum stearate, calcium stearate, magnesium stearate, zinc myristate, magnesium myristate, zinc cetylphosphate, calcium cetylphosphate, and sodium cetylphosphate zinc.

Illustrative example of the color pigment includes an inorganic red pigment such as iron oxide, iron hydroxide, and iron titanate; an inorganic brown pigment such as γ-iron oxide; an inorganic yellow pigment such as a yellow iron oxide and a yellow earth; an inorganic black pigment such as a black iron oxide and a carbon black; an inorganic purple pigment such as a manganese violet and a cobalt violet; an inorganic green pigment such as chromium hydroxide, chromium oxide, cobalt oxide, and cobalt titanate; an inorganic blue pigment such as Prussian blue and azurite; a laked tar dye; a laked natural dye; and a synthetic resin powder obtained by hybridization of these powders.

Illustrative example of the pearl pigment includes a mica coated with titanium oxide, titanium oxide-coated mica, oxychloro bismuth, oxychloro bismuth coated with titanium oxide, a talc coated with titanium oxide, an argentine, and a color mica coated with titanium oxide.

Illustrative example of the metal powder pigment includes an aluminum powder, a copper powder, and a stainless powder.

Illustrative example of the tar dye includes Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207.

Illustrative example of the natural dye includes carminic acid, laccaic acid, carthamin, brazilin, and crocin.

In addition, usable are a powder obtained by hybridizing, or treating these powders, with a general oil material, a silicone oil, a fluorine-containing compound, a surfactant, and the like; a powder treated with a hydrolyzable silyl group or with an alkyl group having a hydrogen atom directly bonded to a silicon atom; an organopolysiloxane with any one of a linear type and a branched type or both, having a hydrolyzable silyl group or a hydrogen atom directly bonded to a silicon atom; an organopolysiloxane with any one of a linear type and a branched type or both, having a hydrolyzable silyl group or a hydrogen atom directly bonded to a silicon atom and co-modified with a long chain alkyl group; an organopolysiloxane with any one of a linear type and a branched type or both, having a hydrolyzable silyl group or a hydrogen atom directly bonded to a silicon atom and co-modified with a polyoxyalkylene group; an acryl-silicone copolymer having a hydrolyzable silyl group or a hydrogen atom directly bonded to a silicon atom; as appropriate, a mixture of one, or two or more of them.

Amount of these powders to be blended is preferably in the range of 0.1 to 90% by mass, relative to a total amount of the cosmetic. In particular, in the case of a powder-solid cosmetic, the amount to be blended is preferably in the range of 70 to 90% by mass, relative to a total amount of the cosmetic.

The cosmetic of the present invention may also use, depending on the purpose thereof, one, or two or more types of surfactants. As to the surfactants like this, there are an anionic, a cationic, a nonionic and an amphoteric surfactant; and in the present invention, there is no particular restriction, and thus any of them may be used provided that the surfactant is used in a usual cosmetic.

Illustrative example of the anionic surfactant includes a fatty acid soap such as sodium stearate and triethanolamine palmitate, an alkyl ether carboxylic acid and a salt thereof, a condensate between an amino acid and a fatty acid, an alkane sulfonate, an alkene sulfonate, a sulfonate of a fatty acid ester, a sulfonate of a fatty acid amide, a sulfonate of a formalin condensate, an alkyl sulfate ester salt, a sulfate ester salt of a secondary alcohol, a sulfate ester salt of an alkyl and an allyl ether, a sulfate ester salt of a fatty acid ester, a sulfate ester salt of a fatty acid alkylolamide, a sulfate ester salt of a Turkey red oil and so on, an alkyl phosphate salt, an ether phosphate salt, an alkyl allyl ether phosphate salt, an amide phosphate salt, N-acyl lactate salt, N-acyl sarcosinate salt, and an N-acylamino acid activator. Illustrative example of the cationic surfactant includes an alkyl amine salt, a salt of an amine such as polyamine and an aminoalcohol fatty acid derivative; an alkyl quaternary ammonium salt, an aromatic quaternary ammonium salt, a pyridinium salt, and an imidazolium salt.

Illustrative example of the nonionic surfactant includes a sorbitan fatty acid ester, a glycerin fatty acid ester, a polyglycerin fatty acid ester, a propylene glycol fatty acid ester, a polyethylene glycol fatty acid ester, a sucrose fatty acid ester, a methyl glucoside fatty ester, alkyl polyglucoside, a polyoxyethylene alkyl ether, a polyoxypropylene alkyl ether, a polyoxyethylene alkyl phenyl ether, a polyoxyethylene fatty acid ester, a polyoxyethylene sorbitan fatty acid ester, a polyoxyethylene sorbitol fatty acid ester, a polyoxyethylene glycerin fatty acid ester, a polyoxyethylene propylene glycol fatty acid ester, a polyoxyethylene castor oil, a polyoxyethylene cured castor oil, a polyoxyethylene phytostanol ether, a polyoxyethylene phytosterol ether, a polyoxyethylene cholestanol ether, a polyoxyethylene cholesteryl ether, a linear or a branched polyoxyalkylene-modified organopolysiloxane, a linear or a branched organopolysiloxane co-modified with a polyoxyalkylene and an alkyl, a linear or a branched organopolysiloxane modified with a poly glycerin, a linear or a branched organopolysiloxane co-modified with a polyglycerin and an alkyl, an alkanol amide, a sugar ether, and a sugar amide. Illustrative example of the amphoteric surfactant includes a betaine, a phosphatidyl choline, an aminocarboxylic acid salt, an imidazoline derivative, and an amido amine.

Among these surfactants, a linear or a branched organopolysiloxane having a polyoxyalkylene chain or a polyglycerin chain in its molecular structure, or a linear or a branched organopolysiloxane further having a long chain alkyl group having 6 to 20 carbon atoms is preferable.

In these surfactants, the content of a hydrophilic polyoxyalkylene group or a polyglycerin residue group is preferably 10 to 70% by mass, relative to its molecular weight; and in addition, amount thereof to be blended into a cosmetic is preferably 0.1 to 20% by mass, or particularly preferably 0.2 to 10% by mass, relative to a total amount of the cosmetic.

The cosmetic of the present invention may contain, depending on the purpose thereof, one, or two or more types of silicone resins.

The silicone resin is preferably an acryl silicone resin, i.e. a graft or a block copolymer of an acryl and a silicone. It is also possible to use an acryl silicone resin containing in its molecular structure at least one type selected from the group consisting of a pyrrolidone moiety, a long chain alkyl moiety, a polyoxyalkylene moiety, a fluoroalkyl moiety, and an anion moiety such as a carboxylic acid.

The silicone resin is preferably a silicone net-work compound comprising a resin composed of an $R^{1s}_3SiO_{0.5}$ unit and an $SiO_2$ unit; a resin composed of an $R^{1s}_3SiO_{0.5}$ unit and an $R^{1s}_2SiO$ unit, and an $SiO_2$ unit; a resin composed of an $R^{1s}_3SiO_{0.5}$ unit and an $R^{1s}SiO_{1.5}$ unit; a resin composed of an $R^{1s}_3SiO_{0.5}$ unit, an $R^{1s}_2SiO$ unit, and an $R^{1s}SiO_{1.5}$ unit; and a resin composed of an $R^{1s}_3SiO_{0.5}$ unit, an $R^{1s}_2SiO$ unit, an $R^{1s}SiO_{1.5}$ unit, and an $SiO_2$ unit ($R^{1s}$ represents an organic group). It is also possible to use a net-work silicone compound containing in its molecular structure at least one type selected from the group consisting of a pyrrolidone moiety, a long chain alkyl moiety, a polyoxyalkylene moiety, a fluoroalkyl moiety, and an amino moiety. When silicone resins such as an acrylic silicone resin and a net-work silicone compound are used, amount thereof to be blended into a cosmetic is preferably 0.1 to 20% by mass, or more preferably 1 to 10% by mass, relative to a total amount of the cosmetic.

The cosmetic of the present invention may also use, depending on the purpose thereof, one, or two or more types of compositions comprising polyoxyalkylene, or crosslinking organopolysiloxane having no polyglycerin group and an oil material that is a liquid at room temperature. It is preferable that this crosslinking organopolysiloxane swell by absorbing the liquid oil, the amount of which is own weight or more of the crosslinking organopolysiloxane. Here, the liquid oil such as the above-mentioned silicone oil, hydrocarbon oil, ester oil, natural vegetable and animal oil, semi-synthetic oil, and fluorine oil may be used; and illustrative example thereof includes low viscous silicone oil having a viscosity of 0.65 to 100.0 mm²/second (25° C.); a hydrocarbon oil such as a liquid paraffin, squalene, isododecane, and isohexadecane; a glyceride oil such as trioctanoin; an ester oil such as isotridecyl isononanoate, an N-acyl glutamate ester, and lauroyl ester sarcosinate; and a natural vegetable and animal oil such as a macadamia nut oil. In addition, it is preferable that the crosslinking agent of this crosslinking organopolysiloxane have two or more reactive vinyl moieties in its molecule and form a crosslinking structure by reacting with a hydrogen atom directly bonded to a silicon atom. Illustrative example of the crosslinking agent having two or more reactive vinyl moieties in its molecule includes an organopolysiloxane containing two or more vinyl groups in its molecule, and an α,ω-alkenyl diene.

The cosmetic of the present invention may contain, depending on the purpose thereof, one, or two or more types of a silicone-modified olefin wax obtained by an addition reaction of an olefin wax containing an unsaturated group composed of an α-olefin and diene and an organohydrogen polysiloxane containing one or more SiH bonds in one molecule. As to the α-olefin, those having 2 to 12 carbon atoms such as ethylene, propylene, 1-butene, 1-hexene, and 4-methyl-1-pentene are preferable; and as to the diene, butadiene, isoprene, 1,4-hexadiene, vinyl norbornene, ethylidene norbornane, dicyclopentadiene, and so on are preferable. As to the organohydrogen polysiloxane containing the SiH bond, those having a linear structure, a siloxane branched structure, and so on may be used.

The cosmetic of the present invention may be added with a component generally used in a usual cosmetic; illustrative example thereof includes an oil-soluble gelation agent, a resin, an antiperspirant, a UV-absorber, a UV absorbing-scattering agent, a moisturizer, an antibacterial preservative, an antimicrobial agent, a fragrance, a salt, an antioxidant, a pH controller, a chelating agent, an algefacient, an anti-inflammatory agent, a skin care component (a skin-lightening agent, a cell activator, a rough skin-improver, a blood circulation promoter, a skin astringent agent, an antiseborrheic agent, and so on), a vitamin, an amino acid, a nucleic acid, a hormone, a clathrate compound, and a hair-immobilizing agent.

Illustrative example of the oil-soluble gelation agent is selected from the gelation agents including a metal soap such as aluminum stearate, magnesium stearate, and zinc myristate; an amino acid derivative such as N-lauroyl-L-glutamic acid and α,γ-di-n-butyl amine; a dextrin fatty acid ester such as dextrin palmitate ester, dextrin stearate ester, and dextrin 2-ethylhexoate palmitate ester; a sucrose fatty acid ester such as sucrose palmitate ester and sucrose stearate ester; a fructo-oligosaccharide fatty acid ester such as fructo-oligosaccharide stearate ester and fructo-oligosaccharide 2-ethylhexanoate ester; benzylidene derivative of sorbitol such as monobenzylidene sorbitol and dibenzylidene sorbitol; an organic-modified clay mineral such as dimethyl benzyl dodecyl ammonium montmorillonite clay and dimethyl dioctadecyl ammonium montmorillonite clay.

Illustrative example of the antiperspirant is selected from the antiperspirants including aluminum chlorohydrate, aluminum chloride, aluminum sesquichlorohydrate, zirconyl hydroxyl chloride, aluminum zirconium hydroxyl chloride, and an aluminum zirconium glycine complex.

Illustrative example of the UV-absorber includes a benzoic acid UV-absorber such as para-amino benzoic acid; an anthranilic acid UV-absorber such as methyl anthranilate; a salicylic UV-absorber such as methyl salicylate, octyl salicylate, and trimethylcyclohexyl salicylate; a cinnamic acid UV-absorber such as octyl para-methoxy cinnamate; a benzophenone UV-absorber such as 2,4-dihydroxybenzophenone; a urocanic acid UV-absorber such as ethyl urocanate; a dibenzoylmethane UV-absorber such as 4-t-butyl-4'-methoxydibenzoylmethane; phenyl benzimidazole sulphonic acid; a triazine derivative. Illustrative example of the UV absorbing-scattering agent includes a particle which absorbs and scatters a UV-beam, such as a titanium oxide microparticle, titanium oxide containing an iron microparticle, a zinc oxide microparticle, a cerium oxide microparticle, and a composite material thereof. A dispersed material obtained by dispersing the particle, which absorbs and scatters a UV-beam into an oil material prior to use, may also be used.

Illustrative example of the moisturizer includes glycerin, sorbitol, propylene glycol, dipropylene glycol, 1,3-butylene glycol, pentylene glycol, glucose, xylitol, maltitol, polyethylene glycol, hyaluronic acid, chondroitin sulfate, pyrrolidone carboxylate salt, polyoxyethylene methyl glucoside, polyoxypropylene methyl glucoside, egg yolk lecithin, soybean lecithin, phosphatidyl choline, phosphatidyl ethanolamine, phosphatidyl serine, phosphatidyl glycerol, phosphatidyl inositol, and sphingo phospholipid.

Illustrative example of the antibacterial preservative includes para-oxybenzoate alkyl ester, benzoic acid, sodium benzoate, sorbic acid, potassium sorbate, and phenoxy ethanol. Illustrative example of the antibacterial agent includes benzoic acid, salicylic acid, carbolic acid, sorbic acid, a para-oxybenzoate alkyl ester, p-chloro-m-cresol, hexachlorophen, benzalkonium chloride, chlorhexidine chloride, trichlorocarbanilide, a photosensitive element, and phenoxy ethanol.

As to the fragrance, a natural fragrance and a synthetic fragrance may be mentioned. Illustrative example of the natural fragrance includes a plant fragrance extracted from a flower, a leaf, wood, pericarp, and so on; and an animal fragrance such as a musk and a civet. Illustrative example of the synthetic fragrance includes a hydrocarbon such as monoterpene; an alcohol such as aliphatic alcohol and aromatic alcohol; an aldehyde such as terpene aldehyde and aromatic aldehyde; a ketone such as alicyclic ketone; an ester such as terpene ester; a lactone; a phenol; an oxide; a nitrogen-containing compound; and an acetal, and so on.

Illustrative example of the salt includes an inorganic salt, an organic salt, an amine salt and an amino acid salt. Illustrative example of the inorganic salt includes an inorganic sodium salt such as hydrochloric acid, sulfuric acid, carbonic acid, and nitric acid, a potassium salt, a magnesium salt, a calcium salt, an aluminum salt, a zirconium salt, and zinc salt. Illustrative example of the organic salt includes a salt of an organic acid such as an acetic acid, dehydroacetic acid, citric acid, malic acid, succinic acid, ascorbic acid, and stearic acid. Illustrative example of the amine salt and amino acid salt includes a salt of an amine such as triethanol amine and an amino acid salt such as a glutamate salt. In addition, a salt of hyaluronic acid and chondroitin sulfate, an aluminum zirconium glycine complex, and a neutralized salt obtained by neutralization of an acid and a base used in a cosmetic prescription may be used.

Illustrative example of the antioxidant includes tocopherol, p-t-butylphenol, butyl hydroxyl anisole, dibutyl hydroxyl toluene, and phytic acid. Illustrative example of the pH controller includes lactic acid, citric acid, glycolic acid, succinic acid, tartaric acid, dl-malic acid, potassium carbonate, sodium bicarbonate, and ammonium bicarbonate. Illustrative example of the chelating agent includes alanine, sodium edetate, sodium polyphosphate, sodium metaphosphate, and phosphoric acid. Illustrative example of the algefacient includes L-menthol and camphor. Illustrative example of the anti-inflammatory agent includes allantoin, glycyrrhizinic acid and its salt, glycyrrhetic acid, stearyl glycyrrhetinate, tranexamic acid, and azulene.

Illustrative example of the skin care component includes a skin-lightening agent such as a placenta extract, arbutin, glutathione, and a saxifrage extract; a cell activator such as a royal jelly, a photosensitive element, a cholesterol derivative, and an extract from hemolysed blood of calf; a rough-skin improver; a blood circulation promoter such as nonylic acid warenylamide, benzyl niconinate ester, β-butoxyethyl niconinate ester, capsaicin, zingerone, cantharides tincture, ichthammol, caffeine, tannic acid, α-borneol, niconic acid tocopherol, inositol hexanicotinate, cyclandelate, cinnarizine, tolazoline, acetyl choline, verapamil, cepharanthine, and γ-orizanol; a skin astringent agent such as zinc oxide and tannic acid; and an antiseborrheic agent such as sulfur and thianthol.

Illustrative example of the vitamin includes a vitamin A such as a vitamin A oil, retinol, retinol acetate, and retinol palmitate; a vitamin B including a vitamin B2 such as riboflavin, riboflavin butyrate, and a flavin adenine nucleotide, a vitamin B6 such as pyridoxine hydrochloride salt, pyridoxine dioctanoate, and pyridoxine tripalmitate, a vitamin B12 and its derivative, and vitamin B15 and its derivative; a vitamin C such as L-ascorbic acid, L-ascorbic acid dipalmitate ester, sodium L-ascorbic-2-sulfate, and dipotassium L-ascorbic acid phosphate diester; a vitamin D such as ergocalciferol and cholecalciferol; a vitamin E such as α-tocopherol, β-tocopherol, γ-tocopherol, dl-α-tocopherol acetate, dl-α-tocopherol nicotinate, and dl-α-tocopherol succinate; a vitamin H; a vitamin P; a nicotinic acid such as nicotinic acid, benzyl nicotinate, and a nicotinic acid amide; a pantothenic acid such as calcium pantothenate, D-pantothenyl alcohol, pantothenyl ethyl ether, and acetyl pantothenyl ethyl ether; and biotin.

Illustrative example of the amino acid includes glycine, valine, leucine, isoleucine, serine, threonine, phenylalanine, arginine, lysine, aspartic acid, glutamic acid, cystine, cysteine, methionine, and tryptophan. Illustrative example of the nucleic acid includes deoxyribonucleic acid. Illustrative example of the hormone includes estradiol and ethenyl estradiol.

Illustrative example of the clathrate compound includes cyclodextrin.

As to the hair-immobilizing polymer, an amphoteric polymer, an anionic polymer, a cationic polymer, and a nonionic polymer may be mentioned. Illustrative example of the hair-immobilizing polymer includes a polyvinyl pyrrolidine polymer such as polyvinyl pyrrolidine and vinyl pyrrolidone/vinyl acetate copolymer; an acidic vinyl ether polymer such as methyl vinyl ether/maleic anhydride alkyl half-ester copolymer; an acidic polyvinyl acetate polymer such as vinyl acetate/crotonic acid copolymer; an acidic acryl polymer compound such as a (meta)acrylic acid/alkyl (meta)acrylate copolymer and a (meta)acrylic acid/alkyl (meta)acrylate/alkyl acrylamide copolymer; and an amphoteric acryl polymer such as an N-methacryloylethyl-N,N-dimethyl ammonium/α-N-methylcarboxybetaine/alkyl (meta)acrylate copolymer and hydroxypropyl (meta)acrylate/butylaminoethyl methacrylate/acrylic acid octyl amide copolymer. In addition, a polymer derived from a nature such as cellulose or its derivative, and keratin and collagen or a derivative thereof may be used suitably.

The cosmetic preferably further contains one or more types of a silicone oil, a hydrocarbon oil, a glycol, an ester oil, a glyceride oil, and a UV absorbing-scattering agent as mentioned above.

Accordingly, the cosmetic of the present invention, depending on a purpose there, can contain a different type of additive.

In the present invention, the form of the cosmetic may be a powder, an oil-base, a water-in-oil emulsion, an oil-in-water emulsion, a non-aqueous emulsion, a multi-emulsion such as W/O/W and O/W/O, but the use as a water-in-oil emulsion is the most preferable.

Illustrative example of the cosmetic in the present invention includes a skin care cosmetic such as a beauty lotion, a milky lotion, a cream, a cleansing cream, a pack, an oil liquid, a massage material, a liquid cosmetic, a beauty oil, a cleansing lotion, a deodorant, a hand cream, a lip cream, and a wrinkle concealer; a make-up cosmetic such as a make-up foundation, a concealer, a white powder, a powder foundation, a liquid foundation, a cream foundation, an oil foundation, a rouge, an eye shadow, a mascara, an eye liner, an eye brow, and a lipstick; a hair cosmetic such as a shampoo, a rinse, a treatment, and a setting material; a UV-protective cosmetic such as an antiperspirant, a sunscreen oil, a sunscreen lotion, and a sunscreen cream.

Particularly, a cosmetic containing water in the form of emulsion is suitable as a makeup foundation, a liquid foundation, a sunscreen lotion and a sunscreen cream, and so on.

The cosmetic can be used according to its any purpose of use.

The cosmetic can be in the form of a liquid, an emulsion, a cream, a solid, a paste, a gel, a powder, a press, a multilayer, a mousse, a spray, a stick, a pencil, and so on.

If the cosmetic of the present invention includes a powder, the cosmetic is preferably in the form of a liquid, a paste, or a solid, with the powder being dispersed therein due to favorable handleability.

EXAMPLES

Hereinafter, the present invention will be described in detail with reference to Examples and Comparative Examples, but the present invention is not restricted to the following Examples.

In the beginning, polymers in Synthesis Examples 1 to 15 to be used in Examples and Comparative Examples were prepared. Polymers in Synthesis Examples 1 to 8 are a composition in the form of a paste including a polymer composed of organohydrogen polysiloxane and polyoxyalkylene, and polymers in Synthesis Examples 9 to 15 are a composition in the form of a paste including a polymer composed of organohydrogen polysiloxane and polyglycerin.

SYNTHESIS EXAMPLES

First, polymers in Synthesis Examples 1 to 8 including a polymer composed of organohydrogen polysiloxane and polyoxyalkylene will be described.

Synthesis Example 1

Into a reactor were charged organohydrogen polysiloxane represented by the average composition formula (1) (324.2 g), polyoxyalkylene represented by the average composition formula (2) (53.8 g), dimethyl polysiloxane (162.0 g) with a viscosity of 6 mm$^2$/s (25° C.), ethanol (270.0 g) and an ethanol solution of 3% by mass of chloroplatinic acid (0.3 g); agitated at 60 to 70° C. for 2 hours; and the solvent was removed under reduced pressure to obtain a crosslinking silicone polymer.

Subsequently, after 50 parts by mass of the crosslinking silicone polymer and 90 parts by mass of dimethyl polysiloxane with a viscosity of 6 mm$^2$/s (25° C.) were dispersed and mixed, the product was sufficiently kneaded and swollen by shear force using 3 rolls to obtain a composition in the form of a paste.

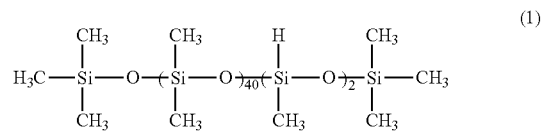

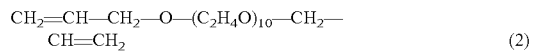

Synthesis Example 2

Into a reactor were charged organohydrogen polysiloxane represented by the average composition formula (3) (611.4 g), polyoxyalkylene represented by the average composition formula (4) (113.7 g), dimethyl polysiloxane (483.4 g) with a viscosity of 10 mm$^2$/s (25° C.), ethanol (600.0 g) and an ethanol solution of 3% by mass of chloroplatinic acid (0.5 g); agitated at 60 to 70° C. for 2 hours; and the solvent was removed under reduced pressure to obtain a crosslinking silicone polymer.

Subsequently, after 36 parts by mass of the crosslinking silicone polymer and 84 parts by mass of dimethyl polysiloxane with a viscosity of 10 mm$^2$/s (25° C.) were dispersed and mixed, the product was sufficiently kneaded and swollen by shear force using 3 rolls to obtain a composition in the form of a paste.

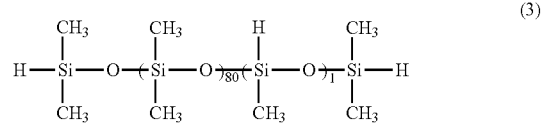

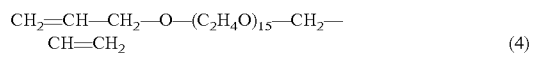

Synthesis Example 3

Into a reactor were charged organohydrogen polysiloxane represented by the average composition formula (5) (529.0 g), polyoxyalkylene represented by the average composition formula (6) (427.6 g), ethanol (240.0 g) and an ethanol solution of 3% by mass of chloroplatinic acid (0.3 g); agitated at 60 to 70° C. for 2 hours; and the solvent was removed under reduced pressure to obtain a crosslinking silicone polymer.

Subsequently, after 30 parts by mass of the crosslinking silicone polymer and 70 parts by mass of squalane were dispersed and mixed, the product was sufficiently kneaded and swollen by shear force using 3 rolls to obtain a composition in the form of a paste.

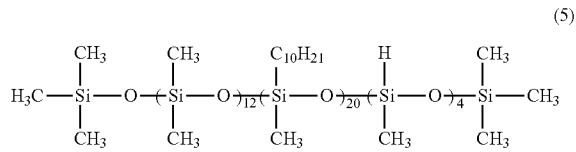

(5)

$CH_2=CH-CH_2-O-(C_2H_4O)_{20}-(C_3H_6O)_{20}-$
$CH_2-CH=CH_2$ (6)

Synthesis Example 4

Into a reactor were charged organohydrogen polysiloxane represented by the average composition formula (7) (756.2 g), polyoxyalkylene represented by the average composition formula (8) (237.6 g), ethanol (150.0 g) and an ethanol solution of 3% by mass of chloroplatinic acid (0.3 g); agitated at 60 to 70° C. for 2 hours; and the solvent was removed under reduced pressure to obtain a crosslinking silicone polymer.

Subsequently, after 25 parts by mass of the crosslinking silicone polymer and 75 parts by mass of cetyl isooctanoate were dispersed and mixed, the product was sufficiently kneaded and swollen by shear force using 3 rolls to obtain a composition in the form of a paste.

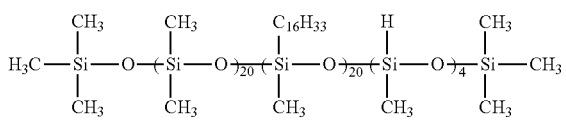

(7)

$CH_2=CH-CH_2-O-(C_2H_4O)_{10}-(C_3H_6O)_5-$
$(C_4H_8O)_5-CH_2-CH=CH_2$ (8)

Synthesis Example 5

Into a reactor were charged organohydrogen polysiloxane represented by the average composition formula (9) (225.4 g), polyoxyalkylene represented by the average composition formula (2) (8.1 g), dimethyl polysiloxane (155.7 g) with a viscosity of 6 mm²/s (25° C.), ethanol (180.0 g) and an ethanol solution of 3% by mass of chloroplatinic acid (0.2 g); agitated at 60 to 70° C. for 2 hours; and the solvent was removed under reduced pressure to obtain a crosslinking silicone polymer.

Subsequently, after 36 parts by mass of the crosslinking silicone polymer and 84 parts by mass of dimethyl polysiloxane with a viscosity of 6 mm²/s (25° C.) were dispersed and mixed, the product was sufficiently kneaded and swollen by shear force using 3 rolls to obtain a composition in the form of a paste.

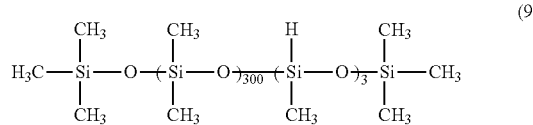

(9)

Synthesis Example 6

Into a reactor were charged organohydrogen polysiloxane represented by the average composition formula (10) (260.6 g), polyoxyalkylene represented by the average composition formula (4) (15.2 g), ethanol (100.0 g) and an ethanol solution of 3% by mass of chloroplatinic acid (0.2 g); agitated at 60 to 70° C. for 2 hours; and the solvent was removed under reduced pressure to obtain a crosslinking silicone polymer.

Subsequently, after 25 parts by mass of the crosslinking silicone polymer and 75 parts by mass of cetyl isooctanoate were dispersed and mixed, the product was sufficiently kneaded and swollen by shear force using 3 rolls to obtain a composition in the form of a paste.

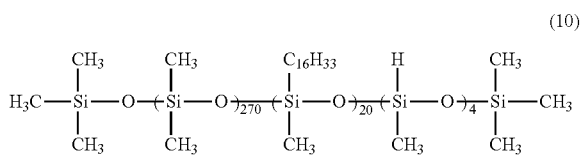

(10)

Synthesis Example 7

Into a reactor were charged organohydrogen polysiloxane represented by the average composition formula (11) (164.7 g), polyoxyalkylene represented by the average composition formula (2) (8.1 g), ethanol (80.0 g) and an ethanol solution of 3% by mass of chloroplatinic acid (0.1 g); agitated at 60 to 70° C. for 2 hours; and the solvent was removed under reduced pressure to obtain a crosslinking silicone polymer.

Subsequently, after 20 parts by mass of the crosslinking silicone polymer and 80 parts by mass of dimethyl polysiloxane with a viscosity of 10⁻²/s (25° C.) were dispersed and mixed, the product was sufficiently kneaded and swollen by shear force using 3 rolls to obtain a composition in the form of a paste.

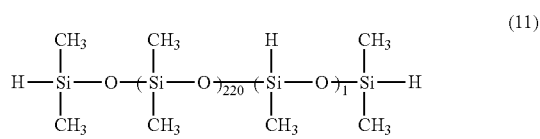

(11)

Synthesis Example 8

Into a reactor were charged organohydrogen polysiloxane represented by the average composition formula (9) (225.4 g), polyoxyalkylene represented by the average composition formula (12) (10.2 g), dimethyl polysiloxane (157.1 g) with a viscosity of 6 mm²/s (25° C.), ethanol (150.0 g) and an ethanol solution of 3% by mass of chloroplatinic acid (0.2 g); agitated at 60 to 70° C. for 2 hours; and the solvent was removed under reduced pressure to obtain a crosslinking silicone polymer.

Subsequently, after 36 parts by mass of the crosslinking silicone polymer and 84 parts by mass of dimethyl polysiloxane with a viscosity of 6 mm²/s (25° C.) were dispersed and mixed, the product was sufficiently kneaded and swollen by shear force using 3 rolls to obtain a composition in the form of a paste.

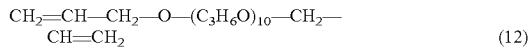
(12)

Calculated values of compositions of crosslinking organopolysiloxane polymers obtained in Synthesis Examples 1 to 8, content of ethylene oxide unit and content of alkylene oxide unit in the polymers will be shown.

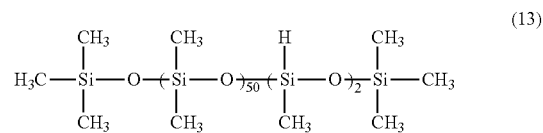
(13)

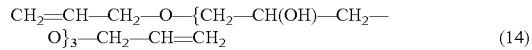
(14)

TABLE 1

| Synthesis Example | Composition corresponding to polymer (B) | | | | Composition corresponding to polymer (A) | | | |
|---|---|---|---|---|---|---|---|---|
|  | 1 | 2 | 3 | 4 | 5 | 6 | 7 | 8 |
| H siloxane molecular weight [A] *1) | 3242 | 6114 | 5290 | 7562 | 22542 | 26062 | 16474 | 22542 |
| PE molecular weight [B] *2) | 538 | 758 | 2138 | 1188 | 538 | 758 | 538 | 678 |
| EO unit content [C] *3) | 440 | 660 | 880 | 440 | 440 | 660 | 440 | 0 |
| POE unit content [D] *4) | — | — | — | — | 440 | 660 | 440 | 580 |
| PE/H siloxane ratio [E] *5) | 1.0 | 1.5 | 2.0 | 2.0 | 1.5 | 2.0 | 1.5 | 1.5 |
| EO unit content in crosslinking polymer *6) | 11.6 | 13.7 | 18.4 | 8.85 | 2.83 | 4.79 | 3.82 | 0 |
| POE unit content in crosslinking polymer *7) | — | — | — | — | 2.83 | 4.79 | 3.82 | 3.69 |

*1) Set molecular weight of organohydrogen polysiloxane represented by the average composition formula
*2) Set molecular weight of polyoxyalkylene represented by the average composition formula
*3) Ethylene oxide unit content in polyoxyalkylene represented by the average composition formula
*4) Alkylene oxide unit content in polyoxyalkylene represented by the average composition formula
*5) Charging ratio of polyoxyalkylene and organohydrogen polysiloxane (molar ratio)
*6) Ethylene oxide unit content (% by mass) obtained by the following formula $$\frac{[C] \times [E]}{([B] \times [E] + [A])} \times 100$$

*7) Alkylene oxide unit content (% by mass) obtained by the following formula $$\frac{[D] \times [E]}{([B] \times [E] + [A])} \times 100$$

Next, polymers in Synthesis Examples 9 to 15 including a polymer composed of organohydrogen polysiloxane and polyglycerin will be described.

Synthesis Example 9

Into a reactor were charged organohydrogen polysiloxane represented by the average composition formula (13) (398.2 g), polyglycerin represented by the average composition formula (14) (32.0 g), dimethyl polysiloxane (286.8 g) with a viscosity of 6 mm²/s (25° C.), ethanol (300.0 g) and an ethanol solution of 3% by mass of chloroplatinic acid (0.3 g); agitated at 60 to 70° C. for 2 hours; and the solvent was removed under reduced pressure to obtain a crosslinking silicone polymer.

Subsequently, after 100 parts by mass of the crosslinking silicone polymer and 140 parts by mass of dimethyl polysiloxane with a viscosity of 6 mm²/s (25° C.) were dispersed and mixed, the product was sufficiently kneaded and swollen by shear force using 3 rolls to obtain a composition in the form of a paste.

Synthesis Example 10

Into a reactor were charged organohydrogen polysiloxane represented by the average composition formula (15) (463.4 g), polyglycerin represented by the average composition formula (14) (48.0 g), dimethyl polysiloxane (340.9 g) with a viscosity of 10 mm²/s (25° C.), ethanol (300.0 g) and an ethanol solution of 3% by mass of chloroplatinic acid (0.3 g); agitated at 60 to 70° C. for 2 hours; and the solvent was removed under reduced pressure to obtain a crosslinking silicone polymer.

Subsequently, after 100 parts by mass of the crosslinking silicone polymer and 140 parts by mass of dimethyl polysiloxane with a viscosity of 10 mm²/s (25° C.) were dispersed and mixed, the product was sufficiently kneaded and swollen by shear force using 3 rolls to obtain a composition in the form of a paste.

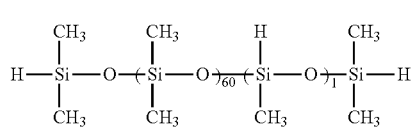

(15)

Synthesis Example 11

Into a reactor were charged organohydrogen polysiloxane represented by the average composition formula (5) (529.0 g), polyglycerin represented by the average composition formula (14) (64.0 g), ethanol (250.0 g) and an ethanol solution of 3% by mass of chloroplatinic acid (0.3 g); agitated at 60 to 70° C. for 2 hours; and the solvent was removed under reduced pressure to obtain a crosslinking silicone polymer.

Subsequently, after 30 parts by mass of the crosslinking silicone polymer and 70 parts by mass of squalane were dispersed and mixed, the product was sufficiently kneaded and swollen by shear force using 3 rolls to obtain a composition in the form of a paste.

Synthesis Example 12

Into a reactor were charged organohydrogen polysiloxane represented by the average composition formula (16) (762.2 g), polyglycerin represented by the average composition formula (17) (117.0 g), ethanol (400.0 g) and an ethanol solution of 3% by mass of chloroplatinic acid (0.5 g); agitated at 60 to 70° C. for 2 hours; and the solvent was removed under reduced pressure to obtain a crosslinking silicone polymer.

Subsequently, after 25 parts by mass of the crosslinking silicone polymer and 75 parts by mass of cetyl isooctanoate were dispersed and mixed, the product was sufficiently kneaded and swollen by shear force using 3 rolls to obtain a composition in the form of a paste.

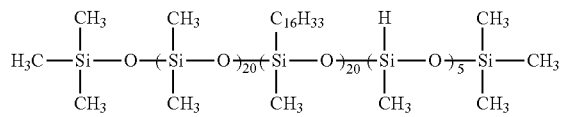

(16)

$CH_2=CH-CH_2-O-\{CH_2-CH(OH)-CH_2-O\}_5-CH_2-CH=CH_2$ (17)

Synthesis Example 13

Into a reactor were charged organohydrogen polysiloxane represented by the average composition formula (18) (151.4 g), polyglycerin represented by the average composition formula (14) (4.8 g), dimethyl polysiloxane (104.1 g) with a viscosity of $6^{-2}/s$ (25° C.), ethanol (100.0 g) and an ethanol solution of 3% by mass of chloroplatinic acid (0.2 g); agitated at 60 to 70° C. for 2 hours; and the solvent was removed under reduced pressure to obtain a crosslinking silicone polymer.

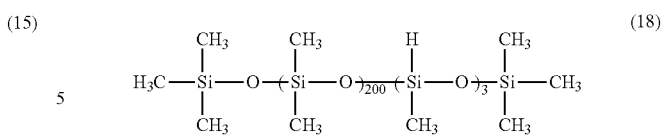

(18)

Subsequently, after 36 parts by mass of the crosslinking silicone polymer and 84 parts by mass of dimethyl polysiloxane with a viscosity of 6 mm²/s (25° C.) were dispersed and mixed, the product was sufficiently kneaded and swollen by shear force using 3 rolls to obtain a composition in the form of a paste.

Synthesis Example 14

Into a reactor were charged organohydrogen polysiloxane represented by the average composition formula (9) (225.4 g), polyglycerin represented by the average composition formula (14) (4.8 g), dimethyl polysiloxane (153.5 g) with a viscosity of 10 mm²/s (25° C.), ethanol (180.0 g) and an ethanol solution of 3% by mass of chloroplatinic acid (0.2 g); agitated at 60 to 70° C. for 2 hours; and the solvent was removed under reduced pressure to obtain a crosslinking silicone polymer.

Subsequently, after 36 parts by mass of the crosslinking silicone polymer and 84 parts by mass of dimethyl polysiloxane with a viscosity of $10^{-2}/s$ (25° C.) were dispersed and mixed, the product was sufficiently kneaded and swollen by shear force using 3 rolls to obtain a composition in the form of a paste.

Synthesis Example 15

Into a reactor were charged organohydrogen polysiloxane represented by the average composition formula (19) (774.2 g), polyglycerin represented by the average composition formula (14) (48.0 g), dimethyl polysiloxane (548.1 g) with a viscosity of 2 mm²/s (25° C.), ethanol (600.0 g) and an ethanol solution of 3% by mass of chloroplatinic acid (0.2 g); agitated at 60 to 70° C. for 2 hours; and the solvent was removed under reduced pressure to obtain a crosslinking silicone polymer.

Subsequently, after 30 parts by mass of the crosslinking silicone polymer and 90 parts by mass of dimethyl polysiloxane with a viscosity of 2 mm²/s (25° C.) were dispersed and mixed, the product was sufficiently kneaded and swollen by shear force using 3 rolls to obtain a composition in the form of a paste.

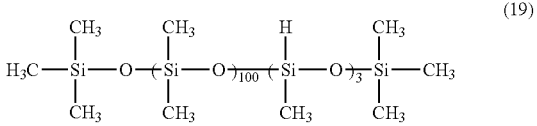

(19)

Calculated values of compositions of crosslinking organopolysiloxane polymers obtained in Synthesis Examples 9 to 15 and content of glycerin unit in the polymers will be shown.

TABLE 2

| Synthesis Example | Composition corresponding to polymer (B) | | | | Composition corresponding to polymer (A) | | |
|---|---|---|---|---|---|---|---|
| | 9 | 10 | 11 | 12 | 13 | 14 | 15 |
| H siloxane molecular weight [A] *1) | 3982 | 4634 | 5290 | 7622 | 15142 | 22542 | 7742 |
| Polyglycerin molecular weight [B] *2) | 320 | 320 | 320 | 468 | 320 | 320 | 320 |
| Glycerin unit content [C] *3) | 222 | 222 | 222 | 370 | 222 | 222 | 222 |
| Polyglycerin/H siloxane ratio [D] *4) | 1.0 | 1.5 | 2.0 | 2.5 | 1.5 | 1.5 | 1.5 |
| Glycerin unit content in crosslinking polymer *5) | 5.16 | 6.51 | 7.49 | 10.5 | 2.13 | 1.45 | 4.05 |

*1) Set molecular weight of organohydrogen polysiloxane represented by the average composition formula
*2) Set molecular weight of polyglycerin represented by the average composition formula
*3) Glycerin unit content in polyglycerin represented by the average composition formula
*4) Charging ratio of polyglycerin and organohydrogen polysiloxane (molar ratio)
*5) Glycerin unit content (% by mass) obtained by the following formula $$\frac{[C] \times [D]}{([B] \times [D] + [A])} \times 100$$

<Comparison of Types of Polymers to be Blended and Combinations>

In the beginning, compositions in the form of a paste including polymers obtained by the above Synthesis Examples 1 to 15 were each used in Comparative Examples 1 to 15. Each of the compositions in the form of a paste corresponding to Synthesis Examples was W/O emulsified according to the following prescription to evaluate the emulsion stability and the playing time for coating a cosmetic on the skin.

(Emulsifying prescription)
(1) A composition in the form of a paste: amount determined so that the amount of a crosslinking polymer is 1.5% by mass
(2) Oil material: amount determined so that the total amount including the composition in the form of a paste is 30% by mass
(3) NaCl: 0.5% by mass
(4) 1,3-BG: 6.0% by mass
(5) Ion-exchanged water: 63.5% by mass Comparative Examples 1 to 8

TABLE 3

| | | | Comparative Example | | | | | | | |
|---|---|---|---|---|---|---|---|---|---|---|
| | | | 1 | 2 | 3 | 4 | 5 | 6 | 7 | 8 |
| Emulsifying composition | Composition in the form of a paste | Synthesis Example 1 | 6.0 | | | | | | | |
| | | Synthesis Example 2 | | 8.3 | | | | | | |
| | | Synthesis Example 3 | | | 5.0 | | | | | |
| | | Synthesis Example 4 | | | | 6.0 | | | | |
| | | Synthesis Example 5 | | | | | 8.3 | | | |
| | | Synthesis Example 6 | | | | | | 6.0 | | |
| | | Synthesis Example 7 | | | | | | | 7.5 | |
| | | Synthesis Example 8 | | | | | | | | 8.3 |
| | Silicone oil *1) | | 24.0 | | | | 21.7 | | | 21.7 |
| | Silicone oil *2) | | | 21.7 | | | | | 22.5 | |
| | Silicone oil *3) | | | | | | | | | |
| | Squalane | | | | 25.0 | | | | | |
| | Cetyl isooctanoate | | | | | 24.0 | | 24.0 | | |
| | NaCl | | 0.5 | 0.5 | 0.5 | 0.5 | 0.5 | 0.5 | 0.5 | 0.5 |
| | 1,3-BG | | 6.0 | 6.0 | 6.0 | 6.0 | 6.0 | 6.0 | 6.0 | 6.0 |
| | Ion-exchanged water | | 63.5 | 63.5 | 63.5 | 63.5 | 63.5 | 63.5 | 63.5 | 63.5 |
| Emulsion stability *4) | | | ○ | ○ | ○ | ○ | x | x | x | x |
| Playing time *5) | | | x | x | x | x | — | — | — | — |

*1) Dimethyl polysiloxane with a viscosity of 6 mm²/s at 25° C.
*2) Dimethyl polysiloxane with a viscosity of 10 mm²/s at 25° C.
*3) Dimethyl polysiloxane with a viscosity of 2 mm²/s at 25° C.
*4) Based on the following criteria
○: Separation is not visually confirmed one month after preserving at 40° C.
Δ: Oil separation is barely visually confirmed one month after preserving at 40° C.

TABLE 3-continued

|  | Comparative Example | | | | | | | |
|---|---|---|---|---|---|---|---|---|
|  | 1 | 2 | 3 | 4 | 5 | 6 | 7 | 8 | x: Oil separation was confirmed within 1 day after preserving it at room temperature

*5) Based on the following criteria

○: Change in strong feeling is found after completion of coating (5 to 10 sec after coating) (playing time is appropriate)

Δ: Only a change in weak feeling is found after completion of coating (5 to 10 sec after coating)

x: Change in strong feeling is found after coating (under 1 to 5 sec after coating) (playing time is too short)

—: Not evaluated due to insufficient emulsion stability

Comparative Examples 9 to 15

TABLE 4

| | | | Comparative Example | | | | | | |
|---|---|---|---|---|---|---|---|---|---|
| | | | 9 | 10 | 11 | 12 | 13 | 14 | 15 |
| Emulsifying composition | Composition in the form of a paste | Synthesis Example 9 | 6.0 | | | | | | |
| | | Synthesis Example 10 | | 6.0 | | | | | |
| | | Synthesis Example 11 | | | 5.0 | | | | |
| | | Synthesis Example 12 | | | | 6.0 | | | |
| | | Synthesis Example 13 | | | | | 8.3 | | |
| | | Synthesis Example 14 | | | | | | 8.3 | |
| | | Synthesis Example 15 | | | | | | | 10.0 |
| | Silicone oil *1) | | 24.0 | | | | 21.7 | | |
| | Silicone oil *2) | | | 24.0 | | | | 21.7 | |
| | Silicone oil *3) | | | | | | | | 20.0 |
| | Squalane | | | | 25.0 | | | | |
| | Cetyl isooctanoate | | | | | 24.0 | | | |
| | NaCl | | 0.5 | 0.5 | 0.5 | 0.5 | 0.5 | 0.5 | 0.5 |
| | 1,3-BG | | 6.0 | 6.0 | 6.0 | 6.0 | 6.0 | 6.0 | 6.0 |
| | Ion-exchanged water | | 63.5 | 63.5 | 63.5 | 63.5 | 63.5 | 63.5 | 63.5 |
| | Emulsion stability *4) | | ○ | ○ | ○ | ○ | x | x | Δ |
| | Playing time *5) | | x | x | x | x | — | — | Δ |

*1) Dimethyl polysiloxane with a viscosity of 6 mm$^2$/s at 25° C.

*2) Dimethyl polysiloxane with a viscosity of 10 mm$^2$/s at 25° C.

*3) Dimethyl polysiloxane with a viscosity of 2 mm$^2$/s at 25° C.

*4) Criteria are the same as above

*5) Criteria are the same as above

The above results found that all of W/O emulsified compositions of Comparative Examples 1 to 15 including only one type of the polymers of the present invention satisfy neither emulsion stability characteristic nor playing time characteristic.

Subsequently, two or more types of compositions in the form of a paste including the polymers obtained by the above Synthesis Examples 1 to 15 were used in Examples 1 to 24, so that the crosslinking organopolysiloxane polymers both having a low and a high content of an ethylene oxide unit and/or a glycerin unit were contained. Each of the compositions in the form of a paste of each Synthesis Examples was W/O emulsified according to the following prescription to evaluate the emulsion stability and the playing time for coating a cosmetic on the skin.

(Emulsifying Prescription)

(1) A composition in the form of a paste: amount determined so that the amount of a crosslinking polymer is 1.5% by mass (2) Oil material: amount determined so that the total amount including the composition in the form of a paste is 30% by mass (3) NaCl: 0.5% by mass (4) 1,3-BG: 6.0% by mass (5) Ion-exchanged water: 63.5% by mass

Examples 1 to 8

TABLE 5

| | | | Example | | | | | | | |
|---|---|---|---|---|---|---|---|---|---|---|
| | | | 1 | 2 | 3 | 4 | 5 | 6 | 7 | 8 |
| Emulsifying composition | Composition in the form of a paste | Synthesis Example 1 | 4.8 | | | | 4.8 | | | |

TABLE 5-continued

| | | | Example | | | | | | | |
|---|---|---|---|---|---|---|---|---|---|---|
| | | | 1 | 2 | 3 | 4 | 5 | 6 | 7 | 8 |
| | | Synthesis Example 2 | | 6.7 | | | | 6.7 | | |
| | | Synthesis Example 3 | | | 4.0 | | | | 4.0 | |
| | | Synthesis Example 4 | | | | 4.8 | | | | 4.8 |
| | | Synthesis Example 5 | 1.7 | | | | | 1.7 | | |
| | | Synthesis Example 6 | | | | 1.2 | | | 1.2 | |
| | | Synthesis Example 7 | | 1.5 | | | 1.5 | | | 0.5 |
| | | Synthesis Example 8 | | | 1.7 | | | | | 1.1 |
| | Silicone oil *1) | | 23.5 | | | | | | | 13.6 |
| | Silicone oil *2) | | | 21.8 | | | | 10.0 | | 5.0 |
| | Silicone oil *3) | | | | | | 23.7 | 11.6 | | 5.0 |
| | Squalane | | | | 24.3 | | | | 14.8 | |
| | Cetyl isooctanoate | | | | | 24.0 | | | 10.0 | |
| | NaCl | | 0.5 | 0.5 | 0.5 | 0.5 | 0.5 | 0.5 | 0.5 | 0.5 |
| | 1,3-BG | | 6.0 | 6.0 | 6.0 | 6.0 | 6.0 | 6.0 | 6.0 | 6.0 |
| | Ion-exchanged water | | 63.5 | 63.5 | 63.5 | 63.5 | 63.5 | 63.5 | 63.5 | 63.5 |
| | Emulsion stability *4) | | ○ | ○ | ○ | ○ | ○ | ○ | ○ | ○ |
| | Playing time *5) | | ○ | ○ | Δ | ○ | ○ | ○ | ○ | Δ |

*1) Dimethyl polysiloxane with a viscosity of 6 mm$^2$/s at 25° C.
*2) Dimethyl polysiloxane with a viscosity of 10 mm$^2$/s at 25° C.
*3) Dimethyl polysiloxane with a viscosity of 2 mm$^2$/s at 25° C.
*4) Criteria are the same as above
*5) Criteria are the same as above Examples 9 to 16

TABLE 6

| | | | Example | | | | | | | |
|---|---|---|---|---|---|---|---|---|---|---|
| | | | 9 | 10 | 11 | 12 | 13 | 14 | 15 | 16 |
| Emulsifying composition | Composition in the form of a paste | Synthesis Example 9 | 4.8 | | | | 4.8 | | | |
| | | Synthesis Example 10 | | 4.8 | | | | 4.8 | | |
| | | Synthesis Example 11 | | | 4.0 | | | 4.0 | | |
| | | Synthesis Example 12 | | | | 4.8 | | | | 4.8 |
| | | Synthesis Example 13 | 1.7 | | | | 1.7 | | | 1.7 |
| | | Synthesis Example 14 | | 1.7 | | | | 1.7 | 1.7 | |
| | | Synthesis Example 15 | | | 2.0 | 2.0 | | | | |
| | Silicone oil *1) | | 23.5 | | | | | 18.5 | | |
| | Silicone oil *2) | | | 23.5 | | | 10.0 | | | |
| | Silicone oil *3) | | | | 24.0 | 23.2 | 13.5 | | | |
| | Squalane | | | | | | | 5.0 | | 10.0 |
| | Cetyl isooctanoate | | | | | | | | 24.3 | 13.5 |
| | NaCl | | 0.5 | 0.5 | 0.5 | 0.5 | 0.5 | 0.5 | 0.5 | 0.5 |
| | 1,3-BG | | 6.0 | 6.0 | 6.0 | 6.0 | 6.0 | 6.0 | 6.0 | 6.0 |
| | Ion-exchanged water | | 63.5 | 63.5 | 63.5 | 63.5 | 63.5 | 63.5 | 63.5 | 63.5 |
| | Emulsion stability *4) | | ○ | ○ | ○ | ○ | ○ | ○ | ○ | ○ |
| | Playing time *5) | | ○ | ○ | ○ | ○ | ○ | ○ | ○ | ○ |

*1) Dimethyl polysiloxane with a viscosity of 6 mm$^2$/s at 25° C.
*2) Dimethyl polysiloxane with a viscosity of 10 mm$^2$/s at 25° C.
*3) Dimethyl polysiloxane with a viscosity of 2 mm$^2$/s at 25° C.
*4) Criteria are the same as above
*5) Criteria are the same as above Examples 17 to 24

TABLE 7

| | | | Example | | | | | | | |
|---|---|---|---|---|---|---|---|---|---|---|
| | | | 17 | 18 | 19 | 20 | 21 | 22 | 23 | 24 |
| Emulsifying composition | Composition in the form of a paste | Synthesis Example 1 | 4.8 | | | | | | 1.2 | 1.2 |
| | | Synthesis Example 3 | | 4.0 | | | | | | |
| | | Synthesis Example 4 | | | 4.8 | | | | | |
| | | Synthesis Example 5 | | | | 1.7 | | | | |
| | | Synthesis Example 6 | | | | | 1.2 | 1.2 | | |
| | | Synthesis Example 9 | | | | 4.8 | | | | |
| | | Synthesis Example 11 | | | | | 4.0 | | | |
| | | Synthesis Example 12 | | | | | | 4.8 | | |
| | | Synthesis Example 13 | 1.7 | | | | | | 6.7 | |
| | | Synthesis Example 14 | | | 1.7 | | | | | 6.7 |
| | | Synthesis Example 15 | | 2.0 | | | | | | |
| | Silicone oil *1) | | 23.5 | | | 13.5 | | 10.0 | | |
| | Silicone oil *2) | | | | | 10.0 | | | 12.1 | 12.1 |
| | Silicone oil *3) | | | 10.0 | 10.0 | | 14.8 | | 5.0 | 5.0 |
| | Squalane | | | 14.0 | | | 5.0 | | | 5.0 |
| | Cetyl isooctanoate | | | | 13.5 | | 5.0 | 14.0 | 5.0 | |
| | NaCl | | 0.5 | 0.5 | 0.5 | 0.5 | 0.5 | 0.5 | 0.5 | 0.5 |
| | 1,3-BG | | 6.0 | 6.0 | 6.0 | 6.0 | 6.0 | 6.0 | 6.0 | 6.0 |
| | Ion-exchanged water | | 63.5 | 63.5 | 63.5 | 63.5 | 63.5 | 63.5 | 63.5 | 63.5 |
| Emulsion stability *4) | | | ○ | ○ | ○ | ○ | ○ | ○ | ○ | ○ |
| Playing time *5) | | | ○ | ○ | ○ | ○ | ○ | ○ | ○ | ○ |

*1) Dimethyl polysiloxane with a viscosity of 6 mm$^2$/s at 25° C.
*2) Dimethyl polysiloxane with a viscosity of 10 mm$^2$/s at 25° C.
*3) Dimethyl polysiloxane with a viscosity of 2 mm$^2$/s at 25° C.
*4) Criteria are the same as above
*5) Criteria are the same as above From the above results, by blending a crosslinking organopolysiloxane polymer having a low content of an oxyalkylene unit and/or a glycerin unit and a crosslinking organopolysiloxane polymer having a high content of an oxyethylene unit and/or a glycerin unit at the same time, a W/O emulsified product that can meet both emulsion stability characteristic and playing time characteristic was obtained.

The above Comparative Examples 1 to 15 and Examples 1 to 24 found that one type of polymers to be blended fails to satisfy both emulsion stability characteristic and playing time characteristic. In addition, by blending two or more types of a crosslinking organopolysiloxane polymer having a low content of an oxyalkylene unit and/or a glycerin unit and a crosslinking organopolysiloxane polymer having a high content of an oxyethylene unit and/or a glycerin unit, an emulsified product that can meet targeted characteristics can be obtained.

<Comparison of Blending Ratios of Polymers>

Moreover, in order to examine the mass ratio of containing a crosslinking organopolysiloxane polymer having a low content of an oxyalkylene unit and/or a glycerin unit and a crosslinking organopolysiloxane polymer having a high content of an oxyethylene unit and/or a glycerin unit, a W/O emulsified composition was adjusted according to the following prescription to evaluate the emulsion stability and the playing time.

(1) A composition in the form of a paste: amount determined so that the amount of a crosslinking polymer is 2.0% by mass
(2) Oil material: amount determined so that the total amount including the composition in the form of a paste is 30.5% by mass
(3) NaCl: 0.5% by mass
(4) 1,3-BG: 6.0% by mass
(5) Ion-exchanged water: 63.0% by mass Examples 25 to 30

TABLE 8

| | | | | Example | | | | | |
|---|---|---|---|---|---|---|---|---|---|
| | | | | 25 | 26 | 27 | 28 | 29 | 30 |
| Emulsifying composition | Composition in the form of a paste | Corresponding to polymer (B) | Synthesis Example 1 | 7.44 | | | 5.60 | 5.60 | |
| | | | Synthesis | | 6.80 | 6.80 | | | 3.60 |

TABLE 8-continued

| | | | Example | | | | | |
|---|---|---|---|---|---|---|---|---|
| | | | 25 | 26 | 27 | 28 | 29 | 30 |
| | | Synthesis Example 9 | | | | | | |
| Corresponding to polymer (A) | | Synthesis Example 5 | 0.78 | | 1.67 | 3.33 | | |
| | | Synthesis Example 13 | | 1.67 | | | 3.33 | 6.11 |
| Oil material | | | 22.28 | 22.03 | 22.03 | 21.57 | 21.57 | 20.79 |
| NaCl | | | 0.5 | 0.5 | 0.5 | 0.5 | 0.5 | 0.5 |
| 1,3-BG | | | 6.0 | 6.0 | 6.0 | 6.0 | 6.0 | 6.0 |
| Ion-exchanged water | | | 63.0 | 63.0 | 63.0 | 63.0 | 63.0 | 63.0 |
| Emulsion stability *1) | | | ○ | ○ | ○ | ○ | ○ | ○ |
| Playing time *2) | | | ○ | ○ | ○ | ○ | ○ | ○ |
| Blending ratio *3) | | | 7:93 | 15:85 | 15:85 | 30:70 | 30:70 | 55:45 |

*1) Criteria are the same as above
*2) Criteria are the same as above
*3) Mass ratio of a crosslinking polymer corresponding to polymer (A) to a crosslinking polymer corresponding to polymer (B)

Comparative Examples 16 to 19

TABLE 9

| | | | | Example | | | |
|---|---|---|---|---|---|---|---|
| | | | | 16 | 17 | 18 | 19 |
| Emulsifying composition | Composition in the form of a paste | Corresponding to polymer (B) | Synthesis Example 1 | 7.68 | | 2.80 | |
| | | | Synthesis Example 9 | | 7.68 | | 2.80 |
| | | Corresponding to polymer (A) | Synthesis Example 5 | 0.44 | | 7.22 | |
| | | | Synthesis Example 13 | | 0.44 | | 7.22 |
| Oil material | | | | 22.28 | 22.38 | 20.48 | 20.48 |
| NaCl | | | | 0.5 | 0.5 | 0.5 | 0.5 |
| 1,3-BG | | | | 6.0 | 6.0 | 6.0 | 6.0 |
| Ion-exchanged water | | | | 63.0 | 63.0 | 63.0 | 63.0 |
| Emulsion stability *1) | | | | ○ | ○ | x | x |
| Playing time *2) | | | | x | x | — | — |
| Blending ratio *3) | | | | 4:96 | 4:96 | 65:35 | 65:35 |

*1) Criteria are the same as above
*2) Criteria are the same as above
*3) Mass ratio of a crosslinking polymer corresponding to polymer (A) to a crosslinking polymer corresponding to polymer (B)

The above results found that in Examples where the ratio of polymer (A) is under 5% and Examples where the ratio of polymer (B) is under 40%, a W/O emulsified product satisfying both emulsion stability characteristic and playing time characteristic was not obtained, so the mass ratio of polymer (A) to polymer (B) is preferably 5:95 to 60:40.

Examples by Use

The following Examples 31 to 50 show Examples by type and use of a cosmetic, but the present invention is not restricted to the following Examples.

Example 31

W/O milky lotion was prepared according to the following prescription. Amount to be blended is shown by % by mass, and the total amount is defined as 100.

TABLE 10

| No. | Component | Amount blended |
|---|---|---|
| 1 | Composition in the form of a paste obtained in Example 1 | 5.0 |
| 2 | Composition in the form of a paste obtained in Example 5 | 5.0 |
| 3 | Dimethyl polysiloxane (6 mm$^2$/s (25° C.)) | 12.0 |
| 4 | Dimethyl polysiloxane (2 mm$^2$/s (25° C.)) | 10.0 |
| 5 | Triethyl hexanoin | 5.0 |
| 6 | Polyether-modified silicone (Note 1) | 3.0 |
| 7 | 1,3-BG | 5.0 |
| 8 | Preservative | Appropriate |
| 9 | Fragrance | Appropriate |
| 10 | Purified water | Remainder |

(Note 1): Product from Shin-Etsu Chemical Co., Ltd.: KF-6017

(Preparation Method)

A: Components 1 to 6 were uniformly mixed.

B: After mixing components 7 to 10, the product A was added to the same to be emulsified.

The milky lotion thus obtained exhibited non-stickiness, smooth spreadability, favorable cosmetic sustainability, and excellent use feeling.

Example 32

W/O Cream

TABLE 11

| No. | Component | Amount blended |
|---|---|---|
| 1 | Composition in the form of a paste obtained in Example 2 | 5.0 |
| 2 | Composition in the form of a paste obtained in Example 7 | 5.0 |
| 3 | Liquid paraffin | 13.5 |
| 4 | Branched silicone co-modified with alkyl and polyether (Note 2) | 1.5 |
| 5 | Sodium citrate | 0.2 |
| 6 | Propylene glycol | 8.0 |
| 7 | Glycerin | 3.0 |
| 8 | Preservative | Appropriate |
| 9 | Fragrance | Appropriate |
| 10 | Purified water | Remainder |

(Note 2): Product from Shin-Etsu Chemical Co., Ltd.: KF-6038

(Preparation Method)

A: Components 1 to 4 were uniformly mixed.

B: After mixing components 5 to 10, the product A was added thereto to be emulsified.

The cream thus obtained exhibited neither stickiness nor greasiness, smooth spreadability, and excellent use feeling.

Example 33

W/O Cream

TABLE 12

| No. | Component | Amount blended |
|---|---|---|
| 1 | Composition in the form of a paste obtained in Example 4 | 5.0 |
| 2 | Composition in the form of a paste obtained in Example 6 | 4.0 |
| 3 | Liquid paraffin | 13.5 |
| 4 | Macadamia nut oil | 5.0 |
| 5 | Branched silicone co-modified with alkyl and polyether (Note 2) | 0.5 |
| 6 | Hybrid silicone composite powder (Note 3) | 3.0 |
| 7 | Sodium citrate | 0.2 |
| 8 | Propylene glycol | 8.0 |
| 9 | Glycerin | 3.0 |
| 10 | Preservative | Appropriate |
| 11 | Fragrance | Appropriate |
| 12 | Purified water | Remainder |

(Note 3): Product from Shin-Etsu Chemical Co., Ltd.: KSP-100

(Preparation Method)

A: Components 1 to 6 were uniformly mixed.

B: After mixing components 7 to 12, the product A was added thereto to be emulsified.

The cream thus obtained exhibited neither stickiness nor greasiness, smooth spreadability, and excellent use feeling.

Example 34

W/O Milky Lotion

TABLE 13

| No. | | Amount blended |
|---|---|---|
| 1 | Composition in the form of a paste obtained in Example 9 | 6.4 |
| 2 | Composition in the form of a paste obtained in Example 13 | 4.0 |
| 3 | Dimethyl polysiloxane (6 mm$^2$/s (25° C.)) | 12.0 |
| 4 | Tristrimethyl siloxymethylsilane | 10.0 |
| 5 | Isotridecyl isononanoate | 5.0 |
| 6 | 1,3-butylene glycol | 5.0 |
| 7 | Sodium citrate | 0.2 |
| 8 | Preservative | Appropriate |
| 9 | Purified water | Remainder |

(Preparation Method)

A: Components 1 to 5 were uniformly mixed.

B: After mixing components 6 to 9, the product A was added thereto to be emulsified.

The milky lotion thus obtained exhibited neither stickiness nor greasiness, smooth spreadability, and excellent use feeling.

Example 35

W/O Cream

TABLE 14

| No. | Component | Amount blended |
|---|---|---|
| 1 | Composition in the form of a paste obtained in Example 10 | 4.0 |
| 2 | Composition in the form of a paste obtained in Example 14 | 3.0 |
| 3 | Crosslinking silicone composition (Note 4) | 3.0 |
| 4 | Dimethyl polysiloxane (6 mm$^2$/s (25° C.)) | 10.0 |
| 5 | Polyether-modified branched silicone (Note 5) | 0.5 |
| 6 | Dipropylene glycol | 10.0 |
| 7 | Sodium citrate | 0.2 |
| 8 | Ethanol | 5.0 |
| 9 | Preservative | Appropriate |
| 10 | Fragrance | Appropriate |
| 11 | Purified water | Remainder |

(Note 4): Product from Shin-Etsu Chemical Co., Ltd.: KSG-15
(Note 5): Product from Shin-Etsu Chemical Co., Ltd.: KF-6028

(Preparation Method)

A: Components 1 to 5 were uniformly mixed.

B: After mixing components 6 to 11, the product A was added thereto to be emulsified.

The cream thus obtained exhibited neither stickiness nor greasiness, smooth spreadability, and excellent use feeling.

Example 36

W/O Make-Up Foundation

TABLE 15

| No. | Component | Amount blended |
|-----|-----------|----------------|
| 1 | Composition in the form of a paste obtained in Example 1 | 4.0 |
| 2 | Composition in the form of a paste obtained in Example 5 | 2.0 |
| 3 | Crosslinking silicone composition (Note 6) | 3.0 |
| 4 | Polyether-modified branched silicone (Note 5) | 0.5 |
| 5 | Dimethyl polysiloxane (6 mm$^2$/s (25° C.)) | 6.0 |
| 6 | Dimethyl polysiloxane (20 mm$^2$/s (25° C.)) | 2.0 |
| 7 | Decamethyl cyclopentasiloxane | 3.0 |
| 8 | Titanium oxide/cyclopentasiloxane dispersed product (Note 7) | 10.0 |
| 9 | Dipropylene glycol | 5.0 |
| 10 | Sodium citrate | 0.2 |
| 11 | Methyl cellulose (2% aqueous solution) (Note 8) | 2.5 |
| 12 | Ethanol | 3.0 |
| 13 | Preservative | Appropriate |
| 14 | Fragrance | Appropriate |
| 15 | Purified water | Remainder |

(Note 6): Product from Shin-Etsu Chemical Co., Ltd.: KSG-16
(Note 7): Product from Shin-Etsu Chemical Co., Ltd.: SPD-T5
(Note 8): Product from Shin-Etsu Chemical Co., Ltd.: Metolose 65-SH4000

(Preparation Method)
A: Components 1 to 8 were uniformly mixed.
B: After mixing components 9 to 15, the product A was added thereto to be emulsified.

The make-up foundation thus obtained exhibited neither stickiness nor greasiness, smooth spreadability, and excellent use feeling.

Example 37

W/O Cream Foundation

TABLE 16

| No. | Component | Amount blended |
|-----|-----------|----------------|
| 1 | Composition in the form of a paste obtained in Example 1 | 5.0 |
| 2 | Composition in the form of a paste obtained in Example 5 | 6.0 |
| 3 | Polyether-modified silicone (Note 1) | 1.0 |
| 4 | Dimethyl polysiloxane (6 mm$^2$/s (25° C.)) | 3.0 |
| 5 | Dimethyl polysiloxane (2 mm$^2$/s (25° C.)) | 9.0 |
| 6 | Triethyl hexanoin | 5.0 |
| 7 | Neopentylglycol dioctanoate | 2.0 |
| 8 | Spherical polymethylsilsesquioxane powder (Note 8) | 1.5 |
| 9 | Branched silicone co-modified with polyglycerin and alkyl (Note 9) | 2.0 |
| 10 | Pigment treated with alkyl and silicone (Note 10) | 5.0 |
| 11 | Pentylene glycol | 5.0 |
| 12 | NaCl | 0.5 |
| 13 | Sodium citrate | 0.2 |
| 14 | Preservative | Appropriate |
| 15 | Fragrance | Appropriate |
| 16 | Purified water | Remainder |

(Note 8): Product from Shin-Etsu Chemical Co., Ltd.: KMP-590
(Note 9): Product from Shin-Etsu Chemical Co., Ltd.: KF-6105
(Note 10): Product from Shin-Etsu Chemical Co., Ltd.: KF-9909 treated powder (Preparation Method)
A: Components 1 to 4, part of component 5, and components 6 to 8 were uniformly mixed.
B: Components 9 and 10 and remainder of component 5 were mixed.
C: Components 11 to 14, and 16 were mixed and dissolved.
D: The product C was added to the product A to be emulsified.
E: Component 15 and the product B were added to the product D and they were uniformly mixed.

The cream foundation thus obtained exhibited neither stickiness nor greasiness, smooth spreadability, and excellent use feeling.

Example 38

W/O Cream Foundation

TABLE 17

| No. | Component | Amount blended |
|-----|-----------|----------------|
| 1 | Composition in the form of a paste obtained in Example 1 | 3.0 |
| 2 | Composition in the form of a paste obtained in Example 5 | 3.0 |
| 3 | Branched silicone co-modified with polyether and alkyl (Note 2) | 1.0 |
| 4 | Triethyl hexanoin | 2.0 |
| 5 | Cetyl isooctanoate | 5.0 |
| 6 | Isotridecyl isononanoate | 9.0 |
| 7 | Hybrid silicone composite powder (Note 3) | 2.0 |
| 8 | Branched silicone co-modified with polyglycerin and alkyl (Note 11) | 0.6 |
| 9 | Branched silicone co-modified with polyglycerin and alkyl (Note 9) | 0.3 |
| 10 | Pigment treated with alkyl and silicone (Note 10) | 10.0 |
| 11 | 1,3-butylene glycol | 5.0 |
| 12 | Sodium chloride | 0.5 |
| 13 | Sodium citrate | 0.2 |
| 14 | Preservative | Appropriate |
| 15 | Fragrance | Appropriate |
| 16 | Purified water | Remainder |

(Note 11): Product from Shin-Etsu Chemical Co., Ltd.: KF-6100

(Preparation Method)
A: Components 1 to 7 were uniformly mixed.
B: Components 8 to 11 were uniformly mixed.
C: Components 12 to 14 and part of component 16 were mixed and dissolved.
D: The product B was added to a remainder of component 16 and uniformly mixed.
E: The product C was added to the product A to be emulsified.
F: The product D was added to the product E to be emulsified, and finally component 15 was added thereto and uniformly mixed.

The cream foundation thus obtained exhibited neither stickiness nor greasiness, smooth spreadability, and excellent use feeling.

Example 39

W/O Liquid Foundation

TABLE 18

| No. | Component | Amount blended |
|-----|-----------|----------------|
| 1 | Composition in the form of a paste obtained in Example 1 | 3.0 |

TABLE 18-continued

| No. | Component | Amount blended |
|---|---|---|
| 2 | Composition in the form of a paste obtained in Example 5 | 3.0 |
| 3 | Polyether-modified branched silicone (Note 5) | 2.0 |
| 4 | Dimethyl polysiloxane (6 mm$^2$/s (25° C.)) | 6.5 |
| 5 | Decamethyl cyclopentasiloxane | 21.6 |
| 6 | Triethyl hexanoin | 5.0 |
| 7 | Organic modified bentonite | 1.2 |
| 8 | Composition co-modified with acryl and silicone (Note 12) | 1.5 |
| 9 | Pigment treated with alkyl and silicone (Note 10) | 5.0 |
| 10 | Dipropylene glycol | 5.0 |
| 11 | Sodium citrate | 0.2 |
| 12 | Preservative | Appropriate |
| 13 | Fragrance | Appropriate |
| 14 | Purified water | Remainder |

(Note 12): Product from Shin-Etsu Chemical Co., Ltd.: KP-575

A: Components 1 to 4, part of component 5, and components 6 and 7 were uniformly mixed.

B: Components 10 to 12, and 14 were uniformly mixed.

C: Components 8 and 9, and a remainder of component 5 were mixed and dissolved.

D: The product C was added to the product A to be emulsified.

E: Component 13 and the product B were added to the product D and were uniformly mixed.

The liquid foundation thus obtained exhibited neither stickiness nor greasiness, smooth spreadability, and excellent use feeling.

Example 40

W/O Compact Foundation

TABLE 19

| No. | Component | Amount blended |
|---|---|---|
| 1 | Ceresin | 5.5 |
| 2 | Microcrystalline wax | 1.0 |
| 3 | Liquid paraffin | 4.0 |
| 4 | Polypropylene glycol dicaprate | 3.0 |
| 5 | Branched silicone co-modified alkyl and polyether (Note 2) | 1.0 |
| 6 | Composition in the form of a paste obtained in Example 9 | 3.0 |
| 7 | Composition in the form of a paste obtained in Example 13 | 3.0 |
| 8 | Dimethyl polysiloxane (6 mm$^2$/s (25° C.)) | 15.5 |
| 9 | Oil-treated titanium oxide (Note 13) | 10.0 |
| 10 | Pigment | Appropriate |
| 11 | Lecithin | 0.3 |
| 12 | Polyoxyethylene sorbitan monooleate | 0.5 |
| 13 | Dipropylene glycol | 8.0 |
| 14 | Sodium citrate | 0.2 |
| 15 | Purified water | Remainder |

(Note 13): Product from Shin-Etsu Chemical Co., Ltd.: AES-3083 treated titanium oxide (Preparation Method)

A: Components 1 to 8 were uniformly heated and mixed.

B: Components 9 to 13 were uniformly mixed.

C: Components 14 and 15 were mixed, and the product B was added thereto, and uniformly mixed.

D: The product C was added to the product A to be emulsified and fed to a compact container.

The compact foundation thus obtained exhibited neither stickiness nor greasiness, smooth spreadability, and excellent use feeling.

Example 41

W/O Stick Foundation

TABLE 20

| No. | Component | Amount blended |
|---|---|---|
| 1 | Ceresin | 5.5 |
| 2 | Stearyl-modified inulin (Note 14) | 2.0 |
| 3 | Neopentyl glycol dioctanoate | 8.0 |
| 4 | Triethyl hexanoin | 4.0 |
| 5 | Dimethyl polysiloxane (6 mm$^2$/s (25° C.)) | 11.5 |
| 6 | Composition in the form of a paste obtained in Example 9 | 3.0 |
| 7 | Composition in the form of a paste obtained in Example 13 | 3.0 |
| 8 | Branched silicone co-modified alkyl and polyether (Note 2) | 1.5 |
| 9 | Spherical polymethylsilsesquioxane powder (Note 8) | 1.5 |
| 10 | Titanium oxide treated with alkyl and silicone (Note 13) | 10.0 |
| 11 | Pigment treated with alkyl and silicone (Note 15) | Appropriate |
| 12 | Lecithin | 0.2 |
| 13 | Polyoxyethylene sorbitan monooleate | 0.3 |
| 14 | Dipropylene glycol | 8.0 |
| 15 | Sodium citrate | 0.2 |
| 16 | Purified water | Remainder |

(Note 14): Product from Chiba Flour Milling Co., Ltd.: Inulin ISK
(Note 15): Product from Shin-Etsu Chemical Co., Ltd.: AES-3083 treated pigment (Preparation Method)

A: Components 1 to 9 were uniformly heated and mixed.

B: Components 10 to 14 were uniformly mixed.

C: Components 15 and 16 were mixed, and the product B was added thereto and uniformly mixed.

D: The product C was added to the product A to be emulsified and molded.

The stick foundation thus obtained exhibited neither stickiness nor greasiness, smooth spreadability, and excellent use feeling.

Example 42

Cream Eye Color

TABLE 21

| No. | Component | Amount blended |
|---|---|---|
| 1 | Composition in the form of a paste obtained in Example 9 | 3.0 |
| 2 | Composition in the form of a paste obtained in Example 13 | 3.0 |
| 3 | Polyether-modified branched silicone (Note 5) | 2.0 |
| 4 | Dimethyl polysiloxane (6 mm$^2$/s (25° C.)) | 6.5 |
| 5 | Tristrimethyl siloxymethylsilane | 21.6 |
| 6 | Triethyl hexanoin | 5.0 |
| 7 | Organic modified bentonite | 1.2 |
| 8 | Composition co-modified with acryl and silicone (Note 12) | 1.5 |
| 9 | Pigment treated with arkyl and silicone (Note 10) | 5.0 |
| 10 | Dipropylene glycol | 5.0 |
| 11 | Sodium citrate | 0.2 |
| 12 | Preservative | Appropriate |

TABLE 21-continued

| No. | Component | Amount blended |
|---|---|---|
| 13 | Fragrance | Appropriate |
| 14 | Purified water | Remainder |

(Preparation Method)
A: Components 1 to 4, part of component 5, and components 6 and 7 were uniformly mixed.
B: Components 10 to 12, and 14 were uniformly mixed.
C: Components 8 and 9, and a remainder of component 5 were mixed.
D: The product C was added to the product A to be emulsified.
E: Component 13 and the product B were added to the product D and uniformly mixed.

The cream eye color thus obtained exhibited neither stickiness nor greasiness, smooth spreadability, and excellent use feeling.

Example 43

Hair Cream

TABLE 22

| No. | Component | Amount blended |
|---|---|---|
| 1 | Composition in the form of a paste obtained in Example 1 | 3.0 |
| 2 | Composition in the form of a paste obtained in Example 13 | 3.0 |
| 3 | Dimethyl polysiloxane (6 mm$^2$/s (25° C.)) | 5.0 |
| 4 | Dimethyl polysiloxane (2 mm$^2$/s (25° C.)) | 8.0 |
| 5 | Stearyl trymethyl ammonium chloride | 1.5 |
| 6 | Glycerin | 3.0 |
| 7 | Propylene glycol | 5.0 |
| 8 | Hydroxyethyl cellulose | 0.2 |
| 9 | Preservative | Appropriate |
| 10 | Fragrance | Appropriate |
| 11 | Purified water | Remainder |

(Preparation Method)
A: Components 1 to 4 were uniformly mixed.
B: Components 5 to 9, and 11 were uniformly mixed.
C: The product B was added to the product A to be emulsified and component 10 was uniformly mixed.

The hair cream thus obtained exhibited neither stickiness nor greasiness, smooth spreadability, and excellent use feeling.

Example 44

Conditioning Mousse

TABLE 23

| No. | Component | Amount blended |
|---|---|---|
| 1 | Composition in the form of a paste obtained in Example 9 | 3.0 |
| 2 | Composition in the form of a paste obtained in Example 5 | 3.0 |
| 3 | Dimethyl polysiloxane (6 mm$^2$/s (25° C.)) | 2.0 |
| 4 | Crosslinking dimethyl polysiloxane (Note 6) | 0.5 |
| 5 | Glyceryl trioctanoate | 1.5 |
| 6 | Glycerin | 3.0 |
| 7 | Stearyl dimethyl ammonium chloride | 0.5 |
| 8 | Polyoxyethylene cured castor oil | 0.5 |

TABLE 23-continued

| No. | Component | Amount blended |
|---|---|---|
| 9 | Ethanol | 7.0 |
| 10 | Preservative | Appropriate |
| 11 | Fragrance | Appropriate |
| 12 | Purified water | Remainder |
| 13 | Liquefied petroleum gas | 5.0 |

(Preparation Method)
A: Components 1 to 5 were uniformly mixed.
B: Components 6 to 10, and 12 were uniformly mixed.
C: The product B was added to the product A to be emulsified, and after component 11 was uniformly mixed, it was filled in an aerosol can, and component 13 was added thereto.

The conditioning mousse thus obtained exhibited neither stickiness nor greasiness, smooth spreadability, and excellent use feeling.

Example 45

Antiperspirant

TABLE 24

| No. | Component | Amount blended |
|---|---|---|
| 1 | Composition in the form of a paste obtained in Example 1 | 3.0 |
| 2 | Composition in the form of a paste obtained in Example 5 | 3.0 |
| 3 | Dimethyl polysiloxane (2 mm$^2$/s (25° C.)) | 7.0 |
| 4 | Glyceryl trioctanoate | 8.0 |
| 5 | 1,3-butylene glycol | 5.0 |
| 6 | Sodium citrate | 0.2 |
| 7 | Aluminum chlorohydrate | 20.0 |
| 8 | Fragrance | Appropriate |
| 9 | Purified water | Remainder |

(Preparation Method)
A: Components 1 to 4 were uniformly mixed.
B: Components 5, 6, and 9 were mixed, and components 7 and 8 were added thereto and dissolved.
C: The product B was added to the product A to be emulsified.

The antiperspirant thus obtained exhibited neither stickiness nor greasiness, smooth spreadability, and excellent use feeling.

Example 46

Sun-Cut Cream

TABLE 25

| No. | Component | Amount blended |
|---|---|---|
| 1 | Zinc oxide treated with alkyl and silicone (Note 16) | 20.0 |
| 2 | Silicone co-modified with alkyl and polyglycerin (Note 9) | 12.0 |
| 3 | Dimethyl polysiloxane (2 mm$^2$/s (25° C.)) | 20.0 |
| 4 | Neopenthyl glycol dioctanoate | 7.0 |
| 5 | Composition in the form of a paste obtained in Example 1 | 3.0 |
| 6 | Composition in the form of a paste obtained in Example 5 | 3.0 |
| 7 | Branched silicone co-modified with alkyl and polyether (Note 2) | 1.0 |
| 8 | Octyl methoxycinnamate | 3.0 |
| 9 | Sodium citrate | 0.2 |

TABLE 25-continued

| No. | Component | Amount blended |
|---|---|---|
| 10 | Dipropylene glycol | 3.0 |
| 11 | Preservative | Appropriate |
| 12 | Fragrance | Appropriate |
| 13 | Purified water | Remainder |

(Note 16): Product from Shin-Etsu Chemical Co., Ltd.: KF-9909 treated zinc oxide (Preparation Method)
A: Part of component 3, and components 4 to 8 were uniformly mixed.
B: Components 9 to 11, and 13 were uniformly mixed.
C: Components 1 and 2, and a remainder of component 3 were mixed and dispersed.
D: The product B was added to the product A to be emulsified.
E: The product C and component 12 were added and uniformly mixed.

The Sun-cut cream thus obtained exhibited neither stickiness nor greasiness, smooth spreadability, and excellent use feeling.

Example 47

Sun-Cut Milky Lotion

TABLE 26

| No. | Component | Amount blended |
|---|---|---|
| 1 | Dimethyl polysiloxane (6 mm²/s (25° C.)) | 5.0 |
| 2 | Composition in the form of a paste obtained in Example 1 | 3.0 |
| 3 | Glyceryl trioctanoate | 2.0 |
| 4 | Composition in the form of a paste obtained in Example 5 | 3.0 |
| 5 | Polyether-modified silicone (Note 1) | 1.0 |
| 6 | Titanium oxide/decamethyl cyclopentasiloxane dispersed product (Note 7) | 30.0 |
| 7 | Zinc oxide/decamethyl cyclopentasiloxane dispersed product (Note 17) | 30.0 |
| 8 | Dipropylene glycol | 3.0 |
| 9 | Sodium citrate | 0.2 |
| 10 | Preservative | Appropriate |
| 11 | Fragrance | Appropriate |
| 12 | Purified water | Remainder |

(Note 17): Product from Shin-Etsu Chemical Co., Ltd.: SPD-Z5

(Preparation Method)
A: Components 1 to 5 were uniformly mixed.
B: Components 8 to 10, and 12 were uniformly mixed, and added to the product A to be emulsified.
C: Components 6, 7, and 11 were uniformly mixed with the product B.

The Sun-cut milky lotion thus obtained exhibited neither stickiness nor greasiness, smooth spreadability, and excellent use feeling.

Example 48

Sun-Cut Cream

TABLE 27

| No. | Component | Amount blended |
|---|---|---|
| 1 | Composition in the form of a paste obtained in Example 1 | 3.0 |
| 2 | Composition in the form of a paste obtained in Example 5 | 3.0 |

TABLE 27-continued

| No. | Component | Amount blended |
|---|---|---|
| 3 | Polyether-modified silicone (Note 5) | 1.0 |
| 4 | Neopenthyl glycol dioctanoate | 2.0 |
| 5 | Silica (AEROSIL 200) | 0.2 |
| 6 | Titanium oxide/decamethyl cyclopentasiloxane dispersed product (Note 7) | 25.0 |
| 7 | Zinc oxide/decamethyl cyclopentasiloxane dispersed product (Note 17) | 15.0 |
| 8 | 1,3-butylene glycol | 5.0 |
| 9 | Sodium citrate | 0.2 |
| 10 | Preservative | Appropriate |
| 11 | Sodium chloride | 0.5 |
| 12 | Purified water | Remainder |

(Preparation Method)
A: Components 1 to 7 were uniformly mixed.
B: Components 8 to 12 were uniformly mixed.
C: The product B was added to the product A to be emulsified.

The Sun-cut cream thus obtained exhibited neither stickiness nor greasiness, smooth spreadability, and excellent use feeling.

Example 49

Solid in-Oil Polyvalent Alcohol Emulsified Cheek Rouge

TABLE 28

| No. | Component | Amount blended |
|---|---|---|
| 1 | Composition in the form of a paste obtained in Example 1 | 3.0 |
| 2 | Composition in the form of a paste obtained in Example 5 | 3.0 |
| 3 | Dimethyl polysiloxane (2 mm²/s (25° C.)) | 3.0 |
| 4 | Dimethyl polysiloxane (6 mm²/s (25° C.)) | 19.7 |
| 5 | Cetyl isooctanoate | 5.0 |
| 6 | Silicone MQ resin solution (Note 18) | 10.0 |
| 7 | Behenyl-modified acryl silicone resin (Note 19) | 3.0 |
| 8 | Paraffin wax (Melting point: 80° C.) | 9.0 |
| 9 | Dimethyl distearyl ammonium hectorite | 0.3 |
| 10 | Acryl silicone treated powder (Note 20) | 25.0 |
| 11 | Preservative | Appropriate |
| 12 | Fragrance | Appropriate |
| 13 | 1,3-butylene glycol | Remainder |

(Note 18): Product from Shin-Etsu Chemical Co., Ltd.: KF-7312J
(Note 19): Product from Shin-Etsu Chemical Co., Ltd.: KP-562P
(Note 20): Product from Shin-Etsu Chemical Co., Ltd.: KP-574 treated (Preparation Method)
A: Components 1 to 9, and 12 were uniformly mixed.
B: Component 10 was added to the product A and uniformly dispersed.
C: Components 11 and 13 were mixed and heated at 80° C., and it was added to the product B to be emulsified, and cooled after being fed to a plate.

The solid in-oil polyvalent alcohol emulsified cheek rouge thus obtained exhibited neither stickiness nor greasiness, smooth spreadability, and excellent use feeling.

Example 50

Cream Lipstick

TABLE 29

| No. | Component | Amount blended |
|---|---|---|
| 1 | Dextrin palmitate/ethylhexanoate (Note 21) | 9.0 |
| 2 | Triethyl hexanoin | 7.0 |
| 3 | Behenyl-modified acryl silicone resin (Note 19) | 8.0 |
| 4 | Composition in the form of a paste obtained in Example 1 | 3.0 |
| 5 | Composition in the form of a paste obtained in Example 5 | 3.0 |
| 6 | Dimethyl polysiloxane (2 mm$^2$/s (25° C.)) | 35.0 |
| 7 | 1,3-butylene glycol | 4.8 |
| 8 | Purified water | Remainder |
| 9 | Color pigment | 6.0 |
| 10 | Mica | 2.0 |
| 11 | Fragrance | Appropriate |

(Note 21): Product from Chiba Flour Milling Co., Ltd.: Rheopearl TT (Preparation Method)
A: Component 1, part of component 2, and components 3 to 6 were heated and uniformly mixed.
B: Component 9 was mixed with a remainder of component 2, dispersed with a roller, added to the product A, and uniformly mixed.
C: Components 7 and 8 were mixed, added to the product B to be emulsified.
D: Components 10 and 11 were added to the product C.

The cream lipstick thus obtained exhibited neither stickiness nor greasiness, smooth spreadability, and excellent use feeling.

As stated above, the present invention can provide a cosmetic having a large degree of change in feeling and a longer playing time, in which the spreadability of an outer oil phase is favorably provided until the completion of uniformly coating of a cosmetic on the skin and a light feeling due to separation of water phase is certainly given just after completion of coating of a cosmetic for various types and uses.

It must be stated here that the present invention is not restricted to the embodiments shown by Examples. The embodiments shown by Examples are merely examples so that any embodiments composed of substantially the same technical concept as disclosed in the claims of the present invention and expressing a similar effect are included in the technical scope of the present invention.

What is claimed is:

1. A cosmetic comprising a polymer (A) having a content of an oxyalkylene unit and/or a glycerin unit of 0.5% by mass or more and under 5.0% by mass; and a polymer (B) having a content of an oxyethylene unit and/or a glycerin unit of 5.0% by mass or more and 20.0% by mass or less, the polymer (A) and the polymer (B) being a crosslinking organopolysiloxane polymer obtained by reacting organohydrogen polysiloxane having two or more hydrogen atoms bonded to a silicon atom in one molecule and polyoxyalkylene and/or polyglycerin having two or more aliphatic unsaturated bonds in one molecule in the presence of a catalyst for a hydrosilylation reaction, wherein a mass ratio of the polymer (A) to the polymer (B) is 5:95 to 60:40.

2. The cosmetic according to claim 1, wherein the first crosslinking organopolysiloxane polymer of the polymer (A) and the second crosslinking organopolysiloxane polymer of the polymer (B) are each obtained by subjecting an organohydrogen polysiloxane represented by the following general formula (I) and one or more compounds selected from the group consisting of a polyoxyalkylene compound represented by the following general formulae (II), (III), or (IV) and a polyglycerin compound represented by the following general formula (V) to addition polymerization, are insoluble in an organic solvent, and swell by containing a liquid oil, an amount of which is own weight or more of the crosslinking organopolysiloxane polymer, $$R^1{}_a H_c Si_{(4-a-c)/2} \qquad (I)$$

(II)

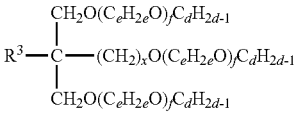

(III)

(IV)

$$C_d H_{2d-1} O(CH_2 CH(OH) CH_2 O)_h C_d H_{2d-1} \qquad (V)$$

wherein each $R^1$ independently represents the same or different substituted or unsubstituted monovalent hydrocarbon group having 1 to 30 carbon atoms having no alkenyl group; $R^3$ represents a substituted or unsubstituted monovalent hydrocarbon group having 1 to 10 carbon atoms having no hydrogen atom or alkenyl group; each $R^4$ independently represents the same or different organic group represented by —$C_d H_{2d-1}$ or the same as $R^3$; "a" and "c" represent a positive number satisfying $1.0 \le a \le 2.3$ and $0.001 \le c \le 1.0$, respectively, and also satisfying $1.5 \le a+c \le 2.6$; "d" represents an integer of 2 to 6; "e" represents an integer of 2 to 4; "f" represents an integer of 1 to 200; "g" represents an integer of 1 to 20; "h" represents an integer of 2 to 10; and "x" represents 0 or 1.

3. The cosmetic according to claim 2, wherein the polymer (A) and the polymer (B) are each obtained by subjecting the organohydrogen polysiloxane (I) and the polyoxyalkylene compound (II) or the polyglycerin compound (V) to addition polymerization, wherein the content of an oxyethylene and/or a glycerin unit in the polymer (A) is 0.5% by mass or more and under 5.0% by mass.

4. The cosmetic according to claim 3, wherein the cosmetic comprises the polymer (A) and the polymer (B), with a total content being 1.0% by mass or more and 50% by mass or less, relative to a total amount of the cosmetic.

5. The cosmetic according to claim 4, wherein the cosmetic further contains water and is in a form of an emulsion.

6. The cosmetic according to claim 3, wherein the cosmetic further contains water and is in a form of an emulsion.

7. The cosmetic according to claim 6, wherein the emulsion is in a form of a water-in-oil.

8. The cosmetic according to claim 3, wherein the cosmetic further contains one or more types of a silicone oil, a hydrocarbon oil, a glycol, an ester oil, a glyceride oil, and a UV absorbing-scattering agent.

9. The cosmetic according to claim 2, wherein the cosmetic comprises the polymer (A) and the polymer (B), with a total content being 1.0% by mass or more and 50% by mass or less, relative to a total amount of the cosmetic.

10. The cosmetic according to claim 9, wherein the cosmetic further contains water and is in a form of an emulsion.

11. The cosmetic according to claim 2, wherein the cosmetic further contains water and is in a form of an emulsion.

12. The cosmetic according to claim 11, wherein the emulsion is in a form of a water-in-oil.

13. The cosmetic according to claim 2, wherein the cosmetic further contains one or more types of a silicone oil, a hydrocarbon oil, a glycol, an ester oil, a glyceride oil, and a UV absorbing-scattering agent.

14. The cosmetic according to claim 2, wherein the cosmetic further contains a powder and is in a form of a liquid, a paste or a solid, with the powder dispersed therein.

15. The cosmetic according to claim 1, wherein the cosmetic comprises the polymer (A) and the polymer (B), with a total content being 1.0% by mass or more and 50% by mass or less, relative to a total amount of the cosmetic.

16. The cosmetic according to claim 15, wherein the cosmetic further contains water and is in a form of an emulsion.

17. The cosmetic according to claim 1, wherein the cosmetic further contains water and is in a form of an emulsion.

18. The cosmetic according to claim 17, wherein the emulsion is in a form of a water-in-oil.

19. The cosmetic according to claim 1, wherein the cosmetic further contains one or more types of a silicone oil, a hydrocarbon oil, a glycol, an ester oil, a glyceride oil, and a UV absorbing-scattering agent.

20. The cosmetic according to claim 1, wherein the cosmetic further contains a powder and is in a form of a liquid, a paste or a solid, with the powder dispersed therein.

* * * * *